US009334509B2

(12) United States Patent
Kawabata et al.

(10) Patent No.: US 9,334,509 B2
(45) Date of Patent: *May 10, 2016

(54) HYDROLASE PROTEIN

(71) Applicant: API CORPORATION, Tokyo (JP)

(72) Inventors: Hiroshi Kawabata, Tokyo (JP); Ryoma Miyake, Yokohama (JP); Kuniko Asada, Tokyo (JP); Ryouhei Katou, Yokohama (JP)

(73) Assignee: API CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/637,429

(22) Filed: Mar. 4, 2015

(65) Prior Publication Data

US 2015/0252393 A1    Sep. 10, 2015

Related U.S. Application Data

(62) Division of application No. 13/813,047, filed as application No. PCT/JP2011/069680 on Aug. 31, 2011, now Pat. No. 9,029,107.

(30) Foreign Application Priority Data

Aug. 31, 2010    (JP) ................. 2010-194630

(51) Int. Cl.
*C12P 7/62* (2006.01)
*C12N 9/18* (2006.01)
*C12P 41/00* (2006.01)
*C12N 9/14* (2006.01)

(52) U.S. Cl.
CPC ... *C12P 7/62* (2013.01); *C12N 9/14* (2013.01); *C12N 9/18* (2013.01); *C12P 41/005* (2013.01); *Y02P 20/52* (2015.11)

(58) Field of Classification Search
None
See application file for complete search history.

(56) References Cited

U.S. PATENT DOCUMENTS

| 5,180,671 | A | 1/1993 | Nishizawa et al. |
| 5,468,632 | A | 11/1995 | Cantwell et al. ............ 435/479 |
| 5,945,325 | A | 8/1999 | Arnold et al. |
| 9,029,107 | B2 | 5/2015 | Kawabata et al. |
| 2008/0233621 | A1 | 9/2008 | Dekishima et al. |
| 2009/0258406 | A1 | 10/2009 | Michels et al. |
| 2013/0096339 | A1 | 4/2013 | Asuma et al. |

FOREIGN PATENT DOCUMENTS

| EP | 0 264 457 | 4/1988 |
| EP | 1 910 532 | 4/2008 |
| JP | 57-134500 | 8/1982 |
| JP | 57-183799 | 11/1982 |
| JP | 58-035197 | 3/1983 |
| JP | 58-67679 | 4/1983 |
| JP | 58-077895 | 5/1983 |
| JP | 58-192900 | 11/1983 |
| JP | 62-244395 | 10/1987 |
| JP | 01-191686 | 8/1989 |
| JP | 02-276575 | 11/1990 |
| JP | 03-210184 | 9/1991 |
| JP | 2009-502184 | 1/2009 |
| WO | 87/06269 | 10/1987 |
| WO | 97/27304 A1 | 7/1997 |
| WO | 2007/017181 | 2/2007 |

OTHER PUBLICATIONS

Fliche et al., "Enantioselective Synthesis of (1R,2S) and (1S,2S) Dehydrocoronamic Acids", *Synth. Commun.*, vol. 24, No. 20, pp. 2873-2876, 1994.
Zimmerman et al., "The Characterization of Amino Acid Sequences in Proteins by Statistical Methods", *J. Theoret. Biol.*, vol. 21, pp. 170-201, 1968.
De Boer et al., "The tac Promoter: A Functional Hybrid Derived From the trp and lac Promoters", *Proc. Natl. Acad. Sci. U.S.A*, vol. 80, pp. 21-25, 1983.
Mandel et al., "Calcium-Dependent Bacteriophage DNA Infection", *J. Mol. Biol.*, vol. 53, pp. 159-162, 1970.
Satoh et al., "Electrotransformation of Intact Cells of *Brevibacterium flavum* MJ-233", *Journal of Industrial Microbiology*, vol. 5, pp. 159-166, 1990.
Ohtsubo, "Transfer-Defective Mutants of Sex Factors in *Escherichia coli*. II. Deletion Mutants of an F-Prime and Deletion Mapping of Cistrons Involved in Genetic Transfer", *Genetics*, vol. 64, pp. 189-197, 1970.
Ottow, "Ecology, Physiology, and Genetics of Fimbriae and Pili", *Ann. Rev. Microbiol.*, vol. 29, pp. 79-108, 1975.
Gabor et al., "Parameters Governing Bacterial Regeneration and Genetic Recombination After Fusion of *Bacillus subtilis* Protoplasts", *Journal of Bacteriology*, vol. 137, No. 3, pp. 1346-1353, 1979.
Dolle et al., "Synthesis, Radiosynthesis and In Vivo Preliminary Evaluation of [$^{11}$C]LBT-999, a Selective Radioligand for the Visualisation of the Dopamine Transporter with PET", *Bioorganic & Medicinal Chemistry*, vol. 14, pp. 1115-1125, 2006.
Zock et al., "The *Bacillus subtilis pnbA* Gene Encoding p-Nitrobenzl Esterase: Cloning, Sequence and High-Level Expression in *Escherichia coli*", *Gene*, vol. 151, No. 1-2, pp. 37-43, 1994.
Alupei et al., "Cyclodextrins in Polymer Synthesis: Synthesis and Influence of Methylated β-Cyclodextrin on the Radical Polymerization Behavior of 1,1-Disubstituted 2-Vinylcyclopropane in Aqueous Medium", *Macromol. Rapid Commun.*, vol. 22, No. 16, pp. 1349-1353, 2001.

(Continued)

*Primary Examiner* — Nashaat Nashed
(74) *Attorney, Agent, or Firm* — Greenblum & Bernstein, P.L.C.

(57) ABSTRACT

It is an object of the present invention to provide a novel hydrolase, which is used when dialkyl 2-vinylcyclopropane-1,1-dicarboxylate is hydrolyzed with an enzyme, so as to efficiently obtain (1S,2S)-1-alkoxycarbonyl-2-vinylcyclopropanecarboxylic acid that is useful as an intermediate for synthesizing therapeutic agents for hepatitis C. According to the present invention, there is provided a hydrolase protein, which consists of the amino acid sequence shown in any one of SEQ ID NOS. 2 to 5 and which has activity of catalyzing, at higher selectivity than the protein consisting of the amino acid sequence shown in SEQ ID NO. 1, a reaction of producing (1S,2S)-1-ethoxycarbonyl-2-vinylcyclopropanecarboxylic acid from diethyl 2-vinylcyclopropane-1,1-dicarboxylate.

2 Claims, No Drawings

(56) References Cited

OTHER PUBLICATIONS

Beaulieu et al., "Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease", *J. Org. Chem.*, vol. 70, No. 15, pp. 5869-5879, 2005.

International Search Report for PCT/JP2011/069680, mailed Nov. 29, 2011, along with an English-language translation.

International Preliminary Report on Patentability for PCT/JP2011/069680, mailed Mar. 14, 2013, along with an English-language translation.

Japanese Office Action issued with respect to Japanese Patent Application No. 2011-539573, mailed Nov. 26, 2013.

Moore et al., "Strategies for the in vitro Evolution of Protein Function: Enzyme Evolution by Random Recombination of Improved Sequences" *Journal of Molecular Biology*, vol. 272, No. 3, pp. 336-347, 1997.

Extended European Search Report issued with respect to EP Patent App. No. 11821834.6, dated Feb. 26, 2014.

NCBI Genbank, registration No. ZP_03593235 (publication date as set forth in a Chinese Office Action issued with respect to Chinese Patent Application No. 201180009868.2 is Jan. 24, 2009).

Chinese Office Action issued with respect to Chinese Patent Application No. 201180009868.2, dated Mar. 21, 2014, along with an English language translation.

English language excerption of Japanese Office Action issued with respect to Japanese Patent Application No. 2011-539573, mailed Nov. 26, 2013.

Nthangeni et al. Database EMBL, Accession No. AY692083.

Macek et al., "Phosphoproteome Analysis of *E. coli* Reveals Evolutionary Conservation of Bacterial Ser/Thr/Tyr Phosphorylation" *Molecular & Cellular Proteomics* 7:299-307, 2008.

SEQUENCE LISTING

```
<160> NUMBER OF SEQ ID NOS: 20

<210> SEQ ID NO 1
<211> LENGTH: 489
<212> TYPE: PRT
<213> ORGANISM: Bacillus subtilis

<400> SEQUENCE: 1

Met Thr His Gln Ile Val Thr Thr Gln Tyr Gly Lys Val Lys Gly Thr
 1               5                  10                  15

Thr Glu Asn Gly Val His Lys Trp Lys Gly Ile Pro Tyr Ala Lys Pro
                20                  25                  30
```

-continued

```
Pro Val Gly Gln Trp Arg Phe Lys Ala Pro Glu Pro Glu Val Trp
         35                  40                  45
Glu Asp Val Leu Asp Ala Thr Ala Tyr Gly Ser Ile Cys Pro Gln Pro
     50                  55                  60
Ser Asp Leu Leu Ser Leu Ser Tyr Thr Glu Leu Pro Arg Gln Ser Glu
 65                  70                  75                  80
Asp Cys Leu Tyr Val Asn Val Phe Ala Pro Asp Thr Pro Ser Lys Asn
                     85                  90                  95
Leu Pro Val Met Val Trp Ile His Gly Gly Ala Phe Tyr Leu Gly Ala
                100                 105                 110
Gly Ser Glu Pro Leu Tyr Asp Gly Ser Lys Leu Ala Ala Gln Gly Glu
            115                 120                 125
Val Ile Val Val Thr Leu Asn Tyr Arg Leu Gly Pro Phe Gly Phe Leu
        130                 135                 140
His Leu Ser Ser Phe Asn Glu Ala Tyr Ser Asp Asn Leu Gly Leu Leu
145                 150                 155                 160
Asp Gln Ala Ala Ala Leu Lys Trp Val Arg Glu Asn Ile Ser Ala Phe
                    165                 170                 175
Gly Gly Asp Pro Asp Asn Val Thr Val Phe Gly Glu Ser Ala Gly Gly
                180                 185                 190
Met Ser Ile Ala Ala Leu Leu Ala Met Pro Ala Ala Lys Gly Leu Phe
            195                 200                 205
Gln Lys Ala Ile Met Glu Ser Gly Ala Ser Arg Thr Met Thr Lys Glu
        210                 215                 220
Gln Ala Ala Ser Thr Ser Ala Ala Phe Leu Gln Val Leu Gly Ile Asn
225                 230                 235                 240
Glu Gly Gln Leu Asp Lys Leu His Thr Val Ser Ala Glu Asp Leu Leu
                    245                 250                 255
Lys Ala Ala Asp Gln Leu Arg Ile Ala Glu Lys Glu Asn Ile Phe Gln
                260                 265                 270
Leu Phe Phe Gln Pro Ala Leu Asp Pro Lys Thr Leu Pro Glu Glu Pro
            275                 280                 285
Glu Lys Ala Ile Ala Glu Gly Ala Ala Ser Gly Ile Pro Leu Leu Ile
        290                 295                 300
Gly Thr Thr Arg Asp Glu Gly Tyr Leu Phe Phe Thr Pro Asp Ser Asp
305                 310                 315                 320
Val His Ser Gln Glu Thr Leu Asp Ala Ala Leu Glu Tyr Leu Leu Gly
                    325                 330                 335
Lys Pro Leu Ala Glu Lys Val Ala Asp Leu Tyr Pro Arg Ser Leu Glu
                340                 345                 350
Ser Gln Ile His Met Met Thr Asp Leu Leu Phe Trp Arg Pro Ala Val
            355                 360                 365
Ala Tyr Ala Ser Ala Gln Ser His Tyr Ala Pro Val Trp Met Tyr Arg
        370                 375                 380
Phe Asp Trp His Pro Lys Pro Tyr Asn Lys Ala Phe His Ala
385                 390                 395                 400
Leu Glu Leu Pro Phe Val Phe Gly Asn Leu Asp Gly Leu Glu Arg Met
                    405                 410                 415
Ala Lys Ala Glu Ile Thr Asp Glu Val Lys Gln Leu Ser His Thr Ile
                420                 425                 430
Gln Ser Ala Trp Ile Thr Phe Ala Lys Thr Gly Asn Pro Ser Thr Glu
            435                 440                 445
```

-continued

```
Ala Val Asn Trp Pro Ala Tyr His Glu Glu Thr Arg Glu Thr Leu Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 2
<211> LENGTH: 489
<212> TYPE: PRT
<213> ORGANISM: Bacillus subtilis

<400> SEQUENCE: 2

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Phe Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Val Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Val Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Ala Glu Pro
        275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335
```

```
Lys Pro Leu Ala Glu Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala His Ser His Tyr Ala Pro Val Trp Met Tyr Arg
    370                 375                 380

Phe Asp Trp His Pro Glu Lys Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Val Thr Asp Glu Val Lys Gln Leu Ser His Ser Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr Gln Glu Glu Thr Arg Glu Thr Leu Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 3
<211> LENGTH: 489
<212> TYPE: PRT
<213> ORGANISM: Bacillus subtilis

<400> SEQUENCE: 3

Met Thr His Gln Ile Val Thr Thr His Tyr Gly Lys Val Lys Gly Thr
1               5                   10                  15

Thr Glu Asn Gly Val His Ile Trp Lys Gly Ile Pro Tyr Ala Lys Pro
            20                  25                  30

Pro Ile Gly Gln Leu Arg Phe Lys Ala Pro Glu Pro Pro Glu Val Trp
        35                  40                  45

Glu Asp Ile Leu Asp Ala Thr Ala Tyr Gly Pro Ile Cys Pro Gln Pro
    50                  55                  60

Pro Asp Leu Leu Ser Leu Ser Tyr Ala Glu Leu Pro Gln Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Arg Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
```

```
            210                 215                 220
Lys Ala Ser Thr Ala Ala Phe Leu Gln Val Leu Gly Ile Ser
225                 230                 235                 240

Glu Ser Gln Leu Asp Arg Leu His Thr Val Ser Thr Glu Asp Leu Leu
                    245                 250                 255

Asn Ala Ala Asp Gln Leu Arg Lys Ala Glu Asn Glu Asn Leu Phe Gln
                    260                 265                 270

Leu Leu Phe Gln Pro Ala Leu Asp Pro Lys Thr Leu Pro Ala Glu Pro
                275                 280                 285

Glu Lys Ala Ile Ala Glu Gly Thr Ala Ala Gly Ile Pro Leu Leu Ile
290                 295                 300

Gly Thr Asn Arg Asp Glu Gly Tyr Leu Phe Phe Thr Pro Asp Ser Asp
305                 310                 315                 320

Val His Ser Gln Glu Thr Phe Asp Ala Ala Leu Glu Tyr Leu Leu Gly
                325                 330                 335

Gln Pro Leu Ala Lys Lys Ala Ala Asp Leu Tyr Pro Arg Phe Leu Glu
                340                 345                 350

Ser Gln Ile His Met Met Thr Asp Leu Leu Phe Trp Arg Pro Ala Val
                355                 360                 365

Ala Tyr Ala Ser Ala Gln Ser His Tyr Ala Pro Val Trp Met Tyr Arg
                370                 375                 380

Phe Asp Trp His Ser Asp Lys Pro Pro Tyr Asn Lys Ala Phe His Ala
385                 390                 395                 400

Leu Glu Leu Pro Phe Val Phe Gly Asn Leu Asp Gly Leu Glu Leu Met
                    405                 410                 415

Ala Lys Ala Glu Val Thr Asp Glu Val Lys Gln Leu Phe His Thr Ile
                420                 425                 430

Gln Ser Ala Trp Thr Thr Phe Ala Lys Thr Gly Asn Pro Ser Thr Glu
                435                 440                 445

Asp Val Lys Trp Pro Ala Tyr His Glu Glu Thr Arg Glu Thr Leu Ile
                450                 455                 460

Leu Glu Ser Glu Ile Trp Met Glu Asn Asp Pro Glu Cys Glu Lys Arg
465                 470                 475                 480

Gln Lys Leu Phe Pro Ser Lys Gly Glu
                485

<210> SEQ ID NO 4
<211> LENGTH: 489
<212> TYPE: PRT
<213> ORGANISM: Bacillus subtilis

<400> SEQUENCE: 4

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Arg Pro
                20                  25                  30

Pro Val Gly Pro Leu Arg Phe Lys Ala Pro Glu Pro Pro Glu Ala Trp
            35                  40                  45

Glu Asn Glu Leu Asp Ala Thr Ala Tyr Gly Pro Ile Cys Pro Gln Pro
        50                  55                  60

Ser Asp Leu Leu Ser Leu Ser Tyr Asn Glu Leu Pro Arg Gln Ser Glu
65                  70                  75                  80

Asn Cys Leu Tyr Val Asn Val Phe Ala Pro Asp Thr Pro Ser Gln Asn
                85                  90                  95
```

Leu Pro Val Met Val Trp Ile His Gly Ala Phe Tyr Leu Gly Ala
            100                 105                 110

Gly Ser Glu Pro Leu Phe Asp Gly Ser Arg Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Thr Glu
    210                 215                 220

Lys Ala Ala Ser Thr Ala Ala Ala Phe Leu Gln Val Leu Gly Ile Asn
225                 230                 235                 240

Glu Ser Gln Leu Asp Arg Leu His Thr Val Ser Ala Glu Asp Leu Leu
                245                 250                 255

Lys Ala Ala Asp Lys Leu Arg Lys Ala Glu Asn Glu Asn Leu Phe Gln
            260                 265                 270

Leu Leu Phe Gln Pro Ala Leu Asp Pro Lys Thr Leu Pro Ala Glu Pro
        275                 280                 285

Glu Lys Ala Ile Ala Gly Gly Ala Ala Ala Asp Ile Pro Leu Leu Ile
    290                 295                 300

Gly Thr Asn Arg Asp Glu Gly Tyr Leu Phe Phe Thr Pro Asp Ser Asp
305                 310                 315                 320

Val His Ser Gln Glu Thr Phe Asn Ala Ala Leu Glu Tyr Leu Leu Glu
                325                 330                 335

Gln Pro Leu Ala Lys Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser Gln Tyr Ala Pro Val Trp Met Tyr Arg
    370                 375                 380

Phe Asp Trp His Ser Asp Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Val Thr Asp Glu Val Lys Arg Leu Ser His Thr Ile
            420                 425                 430

Gln Ser Ala Trp Ile Thr Phe Ala Lys Thr Gly Asn Pro Ser Thr Glu
        435                 440                 445

Asp Val Lys Trp Pro Ala Tyr His Glu Glu Thr Arg Gln Thr Leu Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 5
<211> LENGTH: 489
<212> TYPE: PRT

<213> ORGANISM: Bacillus subtilis

<400> SEQUENCE: 5

```
Met Thr His Gln Ile Val Thr Thr Gln Tyr Gly Lys Val Lys Gly Thr
1               5                   10                  15

Thr Glu Asn Ser Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Pro Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Phe Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Phe Leu Gln Val Leu Gly Ile Asn
225                 230                 235                 240

Glu Ser Gln Leu Asp Gln Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Ser Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser His Tyr Ala Pro Val Trp Met Tyr Arg
    370                 375                 380

Phe Asp Trp His Pro Lys Lys Pro Pro Tyr Asn Lys Ala Phe His Ala
385                 390                 395                 400
```

Leu Glu Leu Pro Phe Val Phe Gly Asn Leu Asp Gly Leu Glu Arg Met
             405                 410                 415

Ala Lys Ala Glu Ile Thr Asp Glu Val Lys Gln Leu Ser His Thr Ile
         420                 425                 430

Gln Ser Ala Trp Ile Thr Phe Ala Lys Thr Gly Asn Pro Ser Thr Glu
     435                 440                 445

Ala Val Asn Trp Pro Thr Tyr His Glu Glu Thr Arg Glu Thr Leu Ile
 450                 455                 460

Leu Asp Ser Glu Ile Thr Ile Glu Lys Asp Pro Glu Ser Glu Lys Arg
465                 470                 475                 480

Gln Lys Leu Phe Pro Ser Lys Gly Glu
                485

<210> SEQ ID NO 6
<211> LENGTH: 1470
<212> TYPE: DNA
<213> ORGANISM: Bacillus subtilis

<400> SEQUENCE: 6

```
atgactcatc aaatagtaac gactcaatac ggcaaagtaa aaggcacaac ggaaaacggc      60
gtacataagt ggaaaggcat ccctatgcc aagccgcctg tcggacaatg gcgttttaaa     120
gcacctgagc cgcctgaagt gtgggaagat gtgcttgatg ccacagcgta cggctctatt     180
tgcccgcagc cgtctgattt gctgtcactt tcgtatactg agctgccccg ccagtccgag     240
gattgcttgt atgtcaatgt atttgcgcct gacaccccaa gtaaaaatct tcctgtcatg     300
gtgtggattc acggaggcgc tttttatcta ggagcgggca gtgagccatt gtatgacgga     360
tcaaaacttg cggcacaggg agaagtcatt gtcgttacat tgaactatcg gctggggccg     420
tttggctttt tgcacttgtc ttcatttaat gaggcgtatt ctgataacct tgggctttta     480
gaccaagccg ccgcgctgaa atgggtgcga gagaatattt cagcgtttgg cggtgatccc     540
gataacgtaa cagtatttgg agaatccgcc ggcgggatga gcattgccgc gctgcttgct     600
atgcctgcgg caaaaggcct gttccagaaa gcaatcatgg aaagcggcgc ttctcgaacg     660
atgacgaaag aacaagcggc gagcaccctcg gcagccttt tacaggtcct tgggattaac     720
gagggccaac tggataaaat tgcatacggt tctgcgaag atttgctaaa agcggctgat     780
cagcttcgga ttgcagaaaa agaaaatatc tttcagctgt tcttccagcc gcccttgat     840
ccgaaaacgc tgcctgaaga accagaaaaa gcgatcgcag aaggggctgc ttccggtatt     900
ccgctattaa ttggaacaac ccgtgatgaa ggatatttat ttttcacccc ggattcagac     960
gttcattctc aggaaacgct tgatgcagcg ctcgagtatt tactagggaa gccgctggca    1020
gagaaagttg ccgatttgta tccgcgttct ctggaaagcc aaattcatat gatgactgat    1080
ttattatttt ggcgccctgc cgtcgcctat gcatccgcac agtctcatta cgcccctgtc    1140
tggatgtaca ggttcgattg gcacccgaag aagccgccgt acaataaagc gtttcacgca    1200
ttagagcttc ctttttgtctt tggaaatctg acggattgg aacgaatggc aaaagcggag    1260
attacggatg aggtgaaaca gctttctcac acgatacaat cagcgtggat cacgttcgcc    1320
aaaacaggaa acccaagcac cgaagctgtg aattggcctg cgtatcatga agaaacgaga    1380
gagacgctga tttttagactc agagattacg atcgaaaacg atcccgaatc tgaaaaaagg    1440
cagaagctat tcccttcaaa aggagaataa                                     1470
```

<210> SEQ ID NO 7
<211> LENGTH: 1470

```
<212> TYPE: DNA
<213> ORGANISM: Bacillus subtilis

<400> SEQUENCE: 7
atgactcatc aaatagtaac gactcaatac ggcaaagtaa aaggcacaac ggaaaacggc      60
gtacataagt ggaaaggcat ccctatgcc aagccgcctg tcggacaatg gcgttttaaa     120
gcacctgagc cgcctgaagt gtgggaagat gtccttgatg ccacagcgta cggccctgtt    180
tgcccgcagc cgtctgattt gctgtcactt tcgtatactg agctgccccg ccagtccgag    240
gattgcttgt ttgtcaatgt atttgcgcct gacactccaa gccaaaacct gcctgtcatg    300
gtttggattc acggaggcgc ttttatctc ggcgcgggca gtgagccatt gtatgacgga     360
tcaaaacttg cggcgcaggg agaggtcatt gtcgttacac tgaactatcg gctggggccg    420
tttggctttt tgcacttgtc ttcgtttgat gaggcgtatt ccgataacct gggcttta     480 gaccaagtcg ccgcactgaa atgggtgcgg agaatatttt cagcgtttgg cggtgatccc    540
gataacgtaa cagtatttgg agaatccgcc ggcgggatga gcattgccgc gcttctcgct    600
atgcctgcgg caaaaggcct gttccagaaa gcagtcatgg aaagcggcgc ttctcgaacg    660
atgacgaaag aacaagcggc gagcacctcg gcagcctttt tacaggtcct gggattaac    720 gagggccaat tggataaatt gcatacggtt tctgcggaag atttgctaaa agcggccgat    780
cagcttcgga tcgcagaaaa agaaaatatc tttcagctgt tcttccagcc cgcccttgat    840
ccaaaaacgc tgcctgctga accagaaaaa gcgatcgcag aaggggccgc ttccggcatt    900
ccgctattaa tcggaacaac ccgtgatgaa ggatatttat ttttcacccc ggattcagac    960
gttcattctc aggaaacgct tgatgcagcg ctcgagtatt tactagggaa gccgctggca   1020
gagaaagctg ccgatttgta tccgcgttct ctggaaagcc aaattcatat gatgactgat   1080 tgttatttt ggcgccccgc tgtcgcctat gcatccgcac attcccatta tgcccctgtc   1140
tggatgtacc ggttcgattg gcacccggag aagccgccgt acaataaagc gtttcacgca   1200
ttagagcttc cttttgtctt tggaaatctg gacggattag aacgaatggc aaaagcggag   1260
gttacggatg aggtgaaaca gctttctcac tcgatacaat cagcatggat cacattcgcc   1320
aaaacaggaa acccaagcac ggaagctgtg aattggccgg cgtatcagga agaaacaaga   1380
gagacgctga ttttagattc agagattacg atcgaaaacg atcccgaatc tgaaaaagg    1440 cagaagctat tcccttcaaa aggagaataa                                     1470

<210> SEQ ID NO 8
<211> LENGTH: 1470
<212> TYPE: DNA
<213> ORGANISM: Bacillus subtilis

<400> SEQUENCE: 8
atgactcatc aaatagtaac gactcattac ggcaaagtaa aaggcacaac agaaaacggc     60
gtacatatat ggaaaggcat tccttatgca aagccgccta tcggacaatt gcgttttaaa    120
gcaccggagc ccctgaagt gtgggaggac atactggatg caacagcgta cggcccgatt     180
tgcccgcagc cgcctgattt gctgtcactt tcatatgccg agcttcccca gcagtccgag    240
gattgcctgt atgtcaatgt atttgcgcct gacactccga gtcaaaactt gcctgtcatg    300
gtgtggattc acggcggcgc ttttatctc ggcgcgggca gtgagccatt atatgatggg     360
tcaagacttg cagcacaggg agaagtcatt gtcgttacac tgaattatcg tctggggcca    420
tttggatttt tacatttgtc ttcgtttgat gaggcgtatt ccgataacct gggcctgttg    480
```

```
gaccaagccg ccgcactgaa atgggtgcga acaatatct ctgcgtttgg cggtgatcca      540
gataacgtaa cggtatttgg agaatccgca ggcggcatga gcattgccgc actgctcgct      600
atgcctgcgg caaaaggcct tttccagaaa gcgatcatgg aaagcggagc ttcccgaacg      660
atgacgaagg aaaaagcggc aagcaccgcg gcagcctttt tacaggtcct tgggatttcc      720
gagagccaat tggacagatt gcatactgta tctacggaag atttgcttaa tgcggccgat      780
cagcttcgga aagcagaaaa tgaaaatctc tttcagctgc tcttccagcc tgctcttgat      840
ccgaaaacgc tgcctgctga accagaaaaa gcgatcgcag aaggcactgc tgccggcatt      900
ccgctgttaa tcggaacaaa ccgcgatgaa ggatatttat ttttcacccc ggactcagac      960
gttcattctc aggaaacgtt tgatgctgcg cttgagtatt tattagggca gccgctggcc     1020
aagaaagctg ccgatctgta cccacgtttt cttgaaagcc aaattcatat gatgactgat     1080
ttattatttt ggcgcccggc cgtcgcctac gcctccgccc agtcccatta cgcgcctgtt     1140
tggatgtacc ggttcgattg gcattcggat aagccgccgt acaataaagc gtttcacgca     1200
ttagagcttc cttttgtttt tggaaatctg acgggttag aactgatggc aaaagcggag     1260
gttacggatg aggtgaaaca gcttttcac accatacaat cagcatggac cacgttcgcc     1320
aaaacaggaa acccaagcac tgaagatgta aaatggccgg cgtatcatga gaaacgaga      1380
gagacgttga ttttagaatc agagatttgg atggaaaacg atcctgaatg tgaaaaaagg     1440
caaaarctat tcccttcaaa aggagaataa                                     1470

<210> SEQ ID NO 9
<211> LENGTH: 1470
<212> TYPE: DNA
<213> ORGANISM: Bacillus subtilis

<400> SEQUENCE: 9
atgactcatc aaatagtaac gactcaatac ggcaaagtaa aaggcacaac agaaaatggc       60
gtacataaat ggaaaggcat ccctatgcc agaccgcctg tcgggccatt gcgttttaaa      120
gcaccggaac ctccggaagc gtgggagaac gaactggacg caacagcgta cggccctatt      180
tgcccgcagc cgtctgattt gctgtcactt tcgtataatg agctgccccg ccagtctgag      240
aattgcttgt atgtcaatgt atttgcgcct gatactccaa gtcaaaacct gcctgtcatg      300
gtgtggattc acggcggcgc ttttttatct tggagcgggca gtgagccatt attcgatggg      360
tcaagacttg cggcgcaggg agaagtcatt gtcgttacac tgaattatcg actggggccg      420
tttggatttt tacatttgtc ttcgtttgat gaggcgtatt ccgataacct tggtcttttg      480
gaccaagccg ccgcactgaa atgggtgcga acaatatct cagcatttgg cggtgatccg      540
gataacgtaa cggtatttgg agaatccgct ggcggcatga gcattgccgc gctgctcgca      600
atgcctgcgg caaaaggcct gttccagaaa gcgatcatgg aaagcggcgc ttctagaaca      660
atgacaacag aaaaagcggc tagcactgca gcagcctttt tacaggtcct tgggattaac      720
gagagccaat tggacagact gcacactgta tctgcggaag atttgcttaa agcggccgat      780
aagcttcgga aagcagaaaa tgaaaatctc tttcagctgt tattccagcc cgcccttgat      840
ccgaaaacgc tgcctgctga accagaaaaa gcaatcgcag gaggtgctgc tgccgacatt      900
ccgctgttaa tcggaacaaa ccgcgatgaa ggatatttat ttttcacccc ggactcagac      960
gttcattctc aagaaacgtt taatgccgcg cttgagtatt tattggaaca gccgctggca     1020
aagaaagccg ccgatctgta tccgcgttca ctagaaagcc aaattcatat gatgactgat     1080
ttgttatttt ggcgcccggc cgtcgcctat gcctccgctc agtctcaata cgcgcctgta     1140
```

```
tggatgtacc gatttgattg gcactctgat aagccgccat acaataaggc gtttcacgca   1200
ttagagcttc cttttgtttt cggaaatctg gacgggttag aacgaatggc aaaagcagag   1260
gttacggatg aggtgaaacg gctttctcat accatacaat cagcatggat cacgtttgcc   1320
aaaacaggaa acccaagcac cgaagatgta aaatggccgg cgtatcatga agaaacaaga   1380
cagacgctga ttttagattc agagattacg atcgaaaacg atcctgaatc tgaaaaaagg   1440
cagaagctat tcccttcaaa aggagaataa                                    1470
```

<210> SEQ ID NO 10
<211> LENGTH: 1470
<212> TYPE: DNA
<213> ORGANISM: Bacillus subtilis

<400> SEQUENCE: 10

```
atgactcatc aaatagtaac gactcaatac ggcaaagtaa agggcacaac ggaaaacagc     60
gtacataagt ggaaaggcat cccctatgcc aagccgcctg tcggacaatg gcgttttaaa    120
gcacctgagc cgcctgaagt gtgggaagat gtccttgatg ccacagcata cggccctatt    180
tgcccgcagc cgtctgattt gctgtcactt tcgtatactg agctgccccg ccagtccgag    240
gattgcttgt ttgtcaatgt atttgcgcct gacactccaa gccaaaacct gcctgtcatg    300
gtttggattc acggaggcgc ttttatctc ggcgcaggca gtgagccatt gtatgacgga    360
tcaaaacttg cggcgcaggg agaggtcatt gtcgttacac tgaactatcg gctggggccg    420
tttggctttt tgcacttgtc ttcatttgat gaggcgtatt ccgataacct tgggctttta   480
gaccaagccg ccgcactgaa atgggtgcgg gagaatatct cagcgtttgg cggtgatccc    540
gataacgtaa cagtatttgg agaatccgcc ggcggcatga gcattgccgc gctgcttgct    600
atgcctgcgg caaaaggcct gttccagaaa gcgatcatgg aaagcggcgc ttcccgaaca    660
atgacaaaag aacaagcggc aagcactgcg gctgcctttt tacaagtcct tggaattaat    720
gagagccagc tggatcaatt gcatacggtt tctgcgaaag atttgctaaa agcggctgat    780
cagcttcgga ttgcagaaaa agaaaatatc tttcagctgt tcttccagcc cgcccttgat    840
ccgaaaacgc tgcctgaaga accagaaaaa gcgatcgcag aagggggctgc ttccggcatt    900 cctctattga ttggaacaac ccgtgatgaa ggatatttat ttttcacccc ggattcagac    960
gttcattctc aggaaacgct tgatgcagcg ctcgagtctt tactagggaa gccgctggca   1020
gagaaagttg ccgatttgta tccgcgttct ctggaaagcc aaattcatat gatgactgat   1080
ttattatttt ggcgccctgc cgtcgcctat gcatccgcac agtctcatta cgcccctgtc   1140
tggatgtaca ggttcgattg gcacccgaag aagccgccgt acaataaagc gtttcacgca   1200
ttagagcttc cttttgtctt tggaaatctg gacggattgg aacgaatggc aaaagcggag   1260
attacggatg aggtgaaaca gctttctcac acgatacaat cagcgtggat cacgttcgcc   1320
aaaacaggaa acccaagcac cgaagctgtg aattggccga cgtatcatga agaaacgaga   1380
gagacgctga ttttagattc agagattacg atcgaaaaag atcccgaatc ggaaaaaagg   1440
cagaagctat tcccttcaaa aggagaataa                                    1470
```

<210> SEQ ID NO 11
<211> LENGTH: 33
<212> TYPE: DNA
<213> ORGANISM: Artificial
<220> FEATURE:
<223> OTHER INFORMATION: PCR primer

<400> SEQUENCE: 11
gcgaattcat gactcatcaa atagtaacga ctc                                    33

<210> SEQ ID NO 12
<211> LENGTH: 33
<212> TYPE: DNA
<213> ORGANISM: Artificial
<220> FEATURE:
<223> OTHER INFORMATION: PCR primer

<400> SEQUENCE: 12
gctctagatt attctccttt tgaagggaat agc                                    33

<210> SEQ ID NO 13
<211> LENGTH: 40
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n; A, T, G or C

<400> SEQUENCE: 13
ccgtctgatt tgctgtcann ktcgtataat gagctgcccc                             40

<210> SEQ ID NO 14
<211> LENGTH: 40
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(22)
<223> OTHER INFORMATION: n; A, T, G or C

<400> SEQUENCE: 14
ggggcagctc attatacgam nntgacagca aatcagacgg                             40

<210> SEQ ID NO 15
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<223> OTHER INFORMATION: n; A, T, G or C
<220> FEATURE:
<221> NAME/KEY: misc_feature
<222> LOCATION: (17)..(18)
<223> OTHER INFORMATION: n; A, T, G or C

<400> SEQUENCE: 15
ccgcgatgaa ggatatnnkt ttttcacccc gg                                     32

<210> SEQ ID NO 16
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (15)..(16)
<223> OTHER INFORMATION: n; A, T, G or C

<400> SEQUENCE: 16
ccggggtgaa aaamnnatat ccttcatcgc gg                               32

<210> SEQ ID NO 17
<211> LENGTH: 53
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (26)..(27)
<223> OTHER INFORMATION: n; A, T, G or C
<220> FEATURE:
<221> NAME/KEY: misc_feature
<222> LOCATION: (35)..(36)
<223> OTHER INFORMATION: n; A, T, G or C

<400> SEQUENCE: 17
gcttcggaaa gcagaaaatg aaaatnnktt tcagnnktta ttccagcccg ccc       53

<210> SEQ ID NO 18
<211> LENGTH: 53
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(19)
<223> OTHER INFORMATION: n; A, T, G or C
<220> FEATURE:
<221> NAME/KEY: misc_feature
<222> LOCATION: (27)..(28)
<223> OTHER INFORMATION: n; A, T, G or C

<400> SEQUENCE: 18
gggcgggctg gaataamnnc tgaaamnnat tttcattttc tgctttccga agc       53

<210> SEQ ID NO 19
<211> LENGTH: 32
<212> TYPE: DNA
<213> ORGANISM: Artificial
<220> FEATURE:
<223> OTHER INFORMATION: PCR primer

<400> SEQUENCE: 19
tccccccggg tcaaggcgca ctcccgttct gg                               32

<210> SEQ ID NO 20
<211> LENGTH: 35
<212> TYPE: DNA
<213> ORGANISM: Artificial
<220> FEATURE:
<223> OTHER INFORMATION: PCR primer

<400> SEQUENCE: 20
tccccccggg tggggtgcct aatgagtgag ctaac                            35

HYDROLASE PROTEIN

This application is a Divisional of U.S. patent application Ser. No. 13/813,047, which is a National Stage of International Application No. PCT/JP2011/069680, filed Aug. 31, 2011, which claims priority to Japanese Application No. 2010-194630, filed Aug. 31, 2010. The disclosures of each of U.S. patent application Ser. No. 13/813,047 and PCT/JP2011/069680 are expressly incorporated by reference herein in their entireties.

TECHNICAL FIELD

The present invention relates to a novel hydrolase protein that can be used in the production of (1S,2S)-1-alkoxycarbonyl-2-vinylcyclopropanecarboxylic acid, and a use thereof.

BACKGROUND ART (1S,2S)-1-alkoxycarbonyl-2-vinylcyclopropanecarboxylic acid is an intermediate that is useful for the production of various types of HCV NS3 protease inhibitors that are currently under development as therapeutic agents for hepatitis C. Non Patent Document 1 describes a method of hydrolyzing dimethyl 2-vinylcyclopropane-1,1-dicarboxylate with an enzyme to obtain (1S,2S)-1-methoxycarbonyl-2-vinylcyclopropanecarboxylic acid. In this method, however, the optical selectivity of the enzyme has been insufficient, and the optical purity of the obtained (1S,2S)-1-methoxycarbonyl-2-vinylcyclopropanecarboxylic acid has been 90% e.e. Thus, this method has been unsuitable as an industrial method for producing an intermediate for medicaments.

The genome sequence of *Bacillus subtilis* ATCC23857 has been known, and the amino acid sequence of para-nitrobenzyl esterase derived from the *Bacillus subtilis* ATCC23857 (which may be hereinafter referred to as "PNBE23857") has been registered under GenBank Accession No. ZP_03593235.

PRIOR ART DOCUMENTS

Non Patent Documents

Non Patent Document 1: C. Fliche et al., Synth. Commun 24(20), 2873-2876 (1994)

SUMMARY OF INVENTION

Object to be Solved by the Invention

It is an object of the present invention to provide a novel hydrolase protein, which is used when dialkyl 2-vinylcyclopropane-1,1-dicarboxylate is hydrolyzed with an enzyme, so as to efficiently obtain (1S,2S)-1-alkoxycarbonyl-2-vinylcyclopropanecarboxylic acid that is useful as an intermediate for producing therapeutic agents for hepatitis C.

Means for Solving the Object

As a result of intensive studies directed towards achieving the aforementioned object, the present inventors have found that a para-nitrobenzyl hydrolase protein derived from *Bacillus subtilis* hydrolyzes diethyl 2-vinylcyclopropane-1,1-dicarboxylate at good selectivity, so as to efficiently obtain (1S,2S)-1-ethoxycarbonyl-2-vinylcyclopropanecarboxylic acid. In addition, the inventors have cloned a para-nitrobenzyl hydrolase gene of a related *Bacillus subtilis*, based on the DNA sequence information of a known *Bacillus subtilis*-derived para-nitrobenzyl hydrolase protein, and they have then confirmed the activity of a para-nitrobenzyl hydrolase protein encoded by the cloned gene. As a result, the inventors have succeeded in obtaining a novel homolog, which catalyzes the above-mentioned hydrolytic reaction at higher selectivity than that of a known para-nitrobenzyl hydrolase protein. Thereafter, the present inventors have performed the homology modeling of the above novel homolog based on the known three-dimensional structure information of the para-nitrobenzyl hydrolase protein, and have conducted a test of introducing mutations into amino acid residues close to a substrate-binding site. As a result, the inventors have succeeded in producing a hydrolase protein, which catalyzes the above-mentioned hydrolytic reaction at much higher selectivity. The present invention has been completed based on these findings.

The present invention provides the following invention.

[1] A hydrolase protein, which consists of the amino acid sequence shown in any one of SEQ ID NOS. 2 to 5, and which has activity of catalyzing, at higher selectivity than the protein consisting of the amino acid sequence shown in SEQ ID NO. 1, the reaction represented by the following formula (1):

[Formula 1]

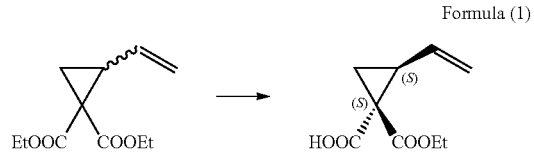

Formula (1)

[2] A hydrolase protein, which consists of an amino acid sequence wherein, in the amino acid sequence shown in any one of SEQ ID NOS. 1 to 5, one or more amino acids at amino acid numbers 70, 106, 107, 108, 219, 270, 271, 272, 273, 274, 275, 276, and 313 are substituted with other amino acids whose side chains have lower bulkiness than that of wild-type amino acids, and which has activity of catalyzing, at higher selectivity than the protein consisting of the amino acid sequence shown in SEQ ID NO. 1, the reaction represented by the following formula (1):

[Formula 2]

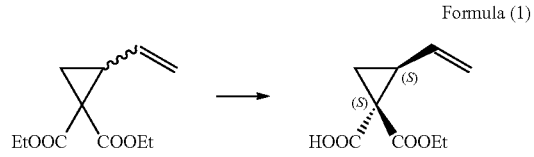

Formula (1)

[3] A hydrolase protein, which consists of an amino acid sequence wherein, in the amino acid sequence shown in any one of SEQ ID NOS. 1 to 5, one or more amino acids at amino acid numbers 188, 190, 193, 215, 216, 217, 314, 358, 362, and 363 are substituted with other amino acids whose side chains have higher bulkiness than that of wild-type amino acids, and which has activity of catalyzing, at higher selectivity than the protein consisting of the amino acid sequence shown in SEQ ID NO. 1, the reaction represented by the following formula (1):

[Formula 3]

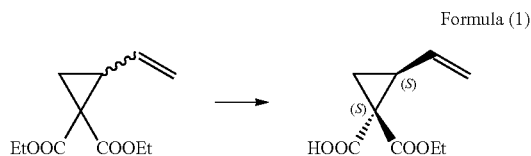

Formula (1)

[4] A hydrolase protein, which consists of an amino acid sequence wherein, in the amino acid sequences shown in any one of SEQ ID NOS. 1 to 5, one or more amino acids at amino acid numbers 70, 106, 107, 108, 219, 270, 271, 272, 273, 274, 275, 276, and 313 are substituted with other amino acids whose side chains have lower bulkiness than that of wild-type amino acids, and one or more amino acids at amino acid numbers 188, 190, 193, 215, 216, 217, 314, 358, 362, and 363 are substituted with other amino acids whose side chains have higher bulkiness than that of wild-type amino acids, and which has activity of catalyzing, at higher selectivity than the protein consisting of the amino acid sequence shown in SEQ ID NO. 1, the reaction represented by the following formula (1):

[Formula 4]

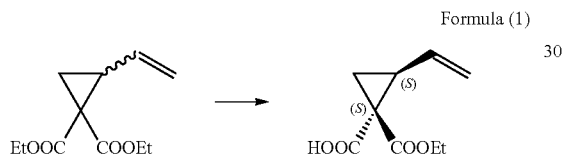

Formula (1)

[5] The hydrolase protein according to [2] or [4], wherein, in the amino acid sequence shown in any one of SEQ ID NOS. 1 to 5, at least one of amino acids at amino acid numbers 70, 270, 273, and 313 is substituted with another amino acid.
[6] The hydrolase protein according to [5], wherein, in the amino acid sequence shown in any one of SEQ ID NOS. 1 to 5, at least the leucine at amino acid number 70 is substituted with any one of aspartic acid, asparagine, serine, threonine, and glycine.
[7] The hydrolase protein according to [5] or [6], wherein, in the amino acid sequence shown in SEQ ID NO. 3 or 4, the leucine at amino acid number 270 is substituted with any one of serine, glutamine, glutamic acid, and alanine.
[8] The hydrolase protein according to [5] or [6], wherein, in the amino acid sequence shown in any one of SEQ ID NOS. 1, 2, and 5, the isoleucine at amino acid number 270 is substituted with any one of serine, glutamine, glutamic acid, and alanine.
[9] The hydrolase protein according to any one of [5] to [8], wherein, in the amino acid sequence shown in any one of SEQ ID NOS. 1 to 5, the leucine at amino acid number 273 is substituted with either arginine or histidine.
[10] The hydrolase protein according to any one of [5] to [9], wherein, in the amino acid sequence shown in any one of SEQ ID NOS. 1 to 5, the leucine at amino acid number 313 is substituted with any one of methionine, alanine, and proline.
[11] A hydrolase protein, which consists of an amino acid sequence wherein, in the amino acid sequence shown in SEQ ID NO. 4, the leucine at amino acid number 70 is substituted with aspartic acid, the leucine at amino acid number 270 is substituted with any one of glutamine, glutamic acid and alanine, the leucine at amino acid number 273 is substituted with arginine, and the leucine at amino acid number 313 is substituted with methionine, and which has activity of catalyzing, at higher selectivity than the protein consisting of the amino acid sequence shown in SEQ ID NO. 1, the reaction represented by the following formula (1):

[Formula 5]

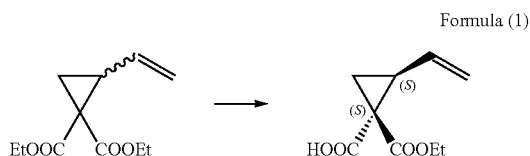

Formula (1)

[12] A hydrolase protein, which consists of an amino acid sequence having homology of 90% or more with the amino acid sequence of the hydrolase protein according to [1] to [11], or an amino acid sequence comprising a substitution, deletion, and/or addition of one or several amino acids with respect to the amino acid sequence of the hydrolase protein according to [1] to [11], and which has activity of catalyzing, at higher selectivity than the protein consisting of the amino acid sequence shown in SEQ ID NO. 1, the reaction represented by the following formula (1):

[Formula 6]

Formula (1)

[13] A DNA encoding the hydrolase protein according to any one of [1] to [12].
[14] The DNA according to [13], which consists of the following nucleotide sequence:
(a) the nucleotide sequence shown in any one of SEQ ID NOS. 7 to 10;
(b) a nucleotide sequence of a DNA capable of hybridizing under stringent conditions with the DNA consisting of the nucleotide sequence shown in any one of SEQ ID NOS. 7 to 10, wherein the nucleotide sequence encodes a hydrolase protein having activity of catalyzing, at higher selectivity than the protein consisting of the amino acid sequence shown in SEQ ID NO. 1, the reaction represented by the following formula (1); or
(c) a nucleotide sequence comprising a substitution, deletion, and/or addition of one or several nucleotides with respect to the nucleotide sequence shown in any one of SEQ ID NOS. 7 to 10, wherein the nucleotide sequence encodes a hydrolase protein having activity of catalyzing, at higher selectivity than the protein consisting of the amino acid sequence shown in SEQ ID NO. 1, the reaction represented by the following formula (1):

[Formula 7]

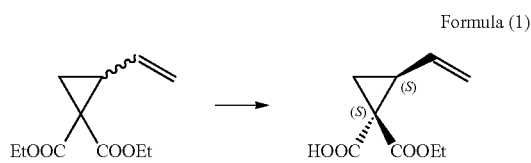

Formula (1)

[15] A method for producing (1S,2S)-1-alkoxycarbonyl-2-vinylcyclopropanecarboxylic acid, which comprises allowing the hydrolase protein according to any one of [1] to [12] to act on dialkyl 2-vinylcyclopropane-1,1-dicarboxylate to produce (1S,2S)-1-alkoxycarbonyl-2-vinylcyclopropanecarboxylic acid.

Effects of Invention

The hydrolase protein of the present invention has high selectivity, and thus, it is able to preferentially generate (1S,2S)-1-alkoxycarbonyl-2-vinylcyclopropanecarboxylic acid, when it hydrolyzes dialkyl 2-vinylcyclopropane-1,1-dicarboxylate to produce 1-alkoxycarbonyl-2-vinylcyclopropanecarboxylic acid. Specifically, according to the hydrolase protein of the present invention, (1S,2S)-1-alkoxycarbonyl-2-vinylcyclopropanecarboxylic acid, which is useful as an intermediate for producing therapeutic agents for hepatitis C, can be produced by an industrially applicable method, more efficiently than conventional methods. A method for producing (1S,2S)-1-alkoxycarbonyl-2-vinylcyclopropanecarboxylic acid using the hydrolase protein of the present invention can be used in production of a therapeutic agent for hepatitis C and an intermediate thereof. The compound produced by the production method of the present invention can be used as a raw material or an intermediate for producing therapeutic agents for hepatitis C.

EMBODIMENTS FOR CARRYING OUT THE INVENTION

Hereinafter, the embodiments for carrying out the present invention will be described in detail.
(1) Hydrolase Protein of the Present Invention The hydrolase protein of the present invention is characterized in that it consists of the amino acid sequence shown in any one of SEQ ID NOS. 2 to 5, or a mutated amino acid sequence thereof, and in that it has activity of catalyzing, at higher selectivity than the protein consisting of the amino acid sequence shown in SEQ ID NO. 1, the reaction represented by the formula (1). Herein, the sequence shown in SEQ ID NO. 1 is the amino acid sequence of para-nitrobenzyl esterase derived from *Bacillus subtilis* ATCC23857 (PNBE23857, GenBank Accession No. ZP_03593235).

[Formula 8]

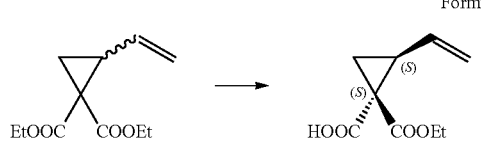

Formula (1)

It is to be noted that Et in the formula (1) represents an ethyl group.

In the present invention, selectivity means optical selectivity, which is a property of preferentially generating a certain isomer so as to generate an optically active compound. Specifically, that is a property of hydrolyzing dialkyl 2-vinylcyclopropane-1,1-dicarboxylate, so as to preferentially generate (1S,2S)-1-alkoxycarbonyl-2-vinylcyclopropanecarboxylic acid.

In order to hydrolyze dialkyl 2-vinylcyclopropane-1,1-dicarboxylate to efficiently obtain (1S,2S)-1-alkoxycarbonyl-2-vinylcyclopropanecarboxylic acid, the following selectivity points are required for the hydrolase protein.
<1R2S/1S2S Ratio>

First of all, dialkyl 2-vinylcyclopropane-1,1-dicarboxylate includes two types of stereoisomers, namely, a (2R) form and a (2S) form. Unless there are special conditions in which stereoinversion occurs at position 2, basically, only the (2S) form can be a raw material for the (1S,2S)-1-alkoxycarbonyl-2-vinylcyclopropanecarboxylic acid of interest.

When the hydrolase protein hydrolyzes dialkyl (2S)-2-vinylcyclopropane-1,1-dicarboxylate, it needs to have selectivity towards preferentially hydrolyzing only a pro-R alkoxycarbonyl group out of two alkoxycarbonyl groups bound to a prochiral carbon at position 1, thereby preferentially generating (1S,2S)-1-alkoxycarbonyl-2-vinylcyclopropanecarboxylic acid. It is to be noted that "pro-R" is a notation for distinguishing two Xs on CX$_2$YZ. The summary of this notation is as follows. The priority of individual substituents on C is determined according to the CIP rules. At the time, it is assumed that one of the two Xs has a higher priority than that of the other X. The priority relationship with Y and Z is not changed. Based on the provisional priority, whether the chirality of central carbon is R or S is determined according to the RS notation. When the chirality is an R form, the preferential X is defined as pro-R. When the chirality is an S form, the preferential X is defined as pro-S.

This selectivity can be subjected to comparison, using, as an indicator, the ratio between the (1S,2S) form and (1R,2S) form in the 1-alkoxycarbonyl-2-vinylcyclopropanecarboxylic acid generated as a result of the hydrolysis. As the ratio of the amount of the (1R,2S) form generated to the amount of the (1S,2S) form generated is decreased, the yield of the (1S,2S)-1-alkoxycarbonyl-2-vinylcyclopropanecarboxylic acid is increased, and thus, it becomes advantageous for industrialization.
<Optical Purity (% e.e.) of 1S2S Form>

When a racemic form of dialkyl 2-vinylcyclopropane-1,1-dicarboxylate is used as a substrate, the (2R) form is hydrolyzed with the hydrolase protein, so as to generate a (1S,2R) form and a (1R,2R) form. At this time, the amount of the generated (1R,2R) form, which is an enantiomer of the (1S,2S) form of interest, is preferably reduced to the minimum. That is to say, the hydrolase protein needs to have selectivity towards preferentially hydrolyzing only a pro-R alkoxycarbonyl group out of two alkoxycarbonyl groups bound to a prochiral carbon at position 1 of dialkyl (2R)-2-vinylcyclopropane-1,1-dicarboxylate, thereby preferentially generating (1S,2R)-1-alkoxycarbonyl-2-vinylcyclopropanecarboxylic acid, and/or selectivity towards preferentially hydrolyzing dialkyl (2S)-2-vinylcyclopropane-1,1-dicarboxylate, rather than dialkyl (2R)-2-vinylcyclopropane-1,1-dicarboxylate. Both of the aforementioned selectivities can be subjected to comparison, using the enantiomer excess (% e.e.) of the (1S,2S) form to the (1R,2R) form in the 1-alkoxycarbonyl-2-vinylcyclopropanecarboxylic acid generated as a result of the hydrolysis. The higher the enantiomer excess of the (1S,2S)

form, the lower the possibility of affecting the subsequent production process or the physiological activity of the produced medicament. Thus, it is advantageous for industrialization.

<1S2R/1S2S Ratio>

As described above, the hydrolase protein hydrolyzes the pro-R alkoxycarbonyl group out of the two alkoxycarbonyl groups bound to a prochiral carbon at position 1 of the dialkyl (2R)-2-vinylcyclopropane-1,1-dicarboxylate, so that it can generate the (1S,2R)-1-alkoxycarbonyl-2-vinylcyclopropanecarboxylic acid that is a diastereomer of the (1S,2S) form of interest. In order to reduce the influence on the subsequent production process, the mixing of this (1S,2R) form is preferably reduced to the minimum.

This selectivity can be subjected to comparison, based on the ratio between the amount of the (1S,2S) form and the amount of the (1S,2R) form in the generated 1-alkoxycarbonyl-2-vinylcyclopropanecarboxylic acid. The lower the ratio of the amount of the (1S,2R) form to the amount of the (1S,2S) form, the lower the possibility of affecting the subsequent production process or the physiological activity of the produced medicament. Thus, it is advantageous for industrialization.

Accordingly, the selectivity in the present invention is based on the indicator that is the "1R2S/1S2S ratio," "optical purity (% e.e.) of the 1S2S form," or "1S2R/1S2S ratio" in the 1-alkoxycarbonyl-2-vinylcyclopropanecarboxylic acid.

That is, the "activity of catalyzing the reaction represented by the formula (1) at higher selectivity than the protein consisting of the amino acid sequence shown in SEQ ID NO. 1" of the present invention can be determined using, as an indicator, the "1R2S/1S2S ratio," "optical purity (% e.e.) of the 1S2S form," or "1S2R/1S2S ratio" in the 1-ethoxycarbonyl-2-vinylcyclopropanecarboxylic acid as a product.

Preferred embodiments of the hydrolase protein of the present invention include the following (a), (b), (c), and (d):

(a) a hydrolase protein, which consists of an amino acid sequence wherein, in the amino acid sequence shown in any one of SEQ ID NOS. 1 to 5, one or more amino acids at amino acid numbers 70, 106, 107, 108, 219, 270, 271, 272, 273, 274, 275, 276, and 313 are substituted with other amino acids whose side chains have lower bulkiness than that of wild-type amino acids, and which has activity of catalyzing the reaction represented by the above formula (1) at higher selectivity than the protein consisting of the amino acid sequence shown in SEQ ID NO. 1;

(b) a hydrolase protein, which consists of an amino acid sequence wherein, in the amino acid sequence shown in any one of SEQ ID NOS. 1 to 5, one or more amino acids at amino acid numbers 188, 190, 193, 215, 216, 217, 314, 358, 362, and 363 are substituted with other amino acids whose side chains have higher bulkiness than that of wild-type amino acids, and which has activity of catalyzing the reaction represented by the above formula (1) at higher selectivity than the protein consisting of the amino acid sequence shown in SEQ ID NO. 1;

(c) a hydrolase protein, which consists of an amino acid sequence wherein, in the amino acid sequences shown in any one of SEQ ID NOS. 1 to 5, one or more amino acids at amino acid numbers 70, 106, 107, 108, 219, 270, 271, 272, 273, 274, 275, 276, and 313 are substituted with other amino acids whose side chains have lower bulkiness than that of wild-type amino acids, and one or more amino acids at amino acid numbers 188, 190, 193, 215, 216, 217, 314, 358, 362, and 363 are substituted with other amino acids whose side chains have higher bulkiness than that of wild-type amino acids, and which has activity of catalyzing the reaction represented by the above formula (1) at higher selectivity than the protein consisting of the amino acid sequence shown in SEQ ID NO. 1; and (d) the hydrolase protein described in (a) or (c) above, which consists of an amino acid sequence in which at least one of amino acids at amino acid numbers 70, 270, 273, and 313 is substituted with another amino acid, and which has activity of catalyzing the reaction represented by the above formula (1) at higher selectivity than the protein consisting of the amino acid sequence shown in SEQ ID NO. 1.

In the present invention, the hydrolase protein described in (d) above is particularly preferable.

With regard to the term "bulkiness" used in the description "amino acids whose side chains have lower bulkiness than that of wild-type amino acids" or "amino acids whose side chains have higher bulkiness than that of wild-type amino acids," the value indicated as "Bulkiness" in Table 3 of J. Theoret. Biol., 1968, 21, 170 can be specifically used as ati indicator. The value of bulkiness of each amino acid is specifically as follows.

Ala (alanine): 11.50
Arg (arginine): 14.28
Asp (aspartic acid): 11.68
Asn (asparagine): 12.82
Cys (cysteine): 13.46
Glu (glutamic acid): 13.57
Gln (glutamine): 14.45
Gly (glycine): 3.40
His (histidine): 13.69
Leu (leucine): 21.40
Ile (isoleucine): 21.40
Lys (lysine): 15.71
Met (methionine): 16.25
Phe (phenylalanine): 19.80
Pro (proline): 17.43
Ser (serine): 9.47
Thr (threonine): 15.77
Trp (tryptophan): 21.67
Tyr (tyrosine): 18.03
Val (valine): 21.57

That is to say, the description "one or more amino acids . . . are substituted with other amino acids whose side chains have lower bulkiness than that of wild-type amino acids" is used to mean that the amino acids are substituted with amino acids each having the above-described bulkiness value that is smaller than that of wild-type amino acids. On the other hand, the description "one or more amino acids . . . are substituted with other amino acids whose side chains have higher bulkiness than that of wild-type amino acids" is used to mean that the amino acids are substituted with amino acids each having the above-described bulkiness value that is larger than that of wild-type amino acids.

In particular, the hydrolase protein of the present invention is preferably a hydrolase protein wherein, in the amino acid sequence shown in any one of SEQ ID NOS. 1 to 5, one or more leucine or isoleucine residues at amino acid numbers 70, 270, 273, and 313 are substituted with amino acids each having the above-described bulkiness value that is smaller than their bulkiness values.

Examples of such a hydrolase protein include the following (e), (f), (g), (h), and (i):

(e) the hydrolase protein described in (d) above, wherein, in the amino acid sequence shown in any one of SEQ ID NOS. 1 to 5, at least the leucine at amino acid number 70 is substituted with any one of aspartic acid, asparagine, serine, threonine, and glycine;

(f) the hydrolase protein described in (d) or (e) above, wherein, in the amino acid sequence shown in SEQ ID NO. 3 or 4, the leucine at amino acid number 270 is substituted with any one of serine, glutamine, glutamic acid, and alanine;

(g) the hydrolase protein described in (d) or (e) above, wherein, in the amino acid sequence shown in any one of SEQ ID NOS. 1, 2, and 5, the isoleucine at amino acid number 270 is substituted with any one of serine, glutamine, glutamic acid, and alanine;

(h) the hydrolase protein described in any one of (d) to (g) above, wherein, in the amino acid sequence shown in any one of SEQ ID NOS. 1 to 5, the leucine at amino acid number 273 is substituted with either arginine or histidine; and (i) the hydrolase protein described in any one of (d) to (h) above, wherein, in the amino acid sequence shown in any one of SEQ ID NOS. 1 to 5, the leucine at amino acid number 313 is substituted with any one of methionine, alanine, and proline.

The hydrolase protein of the present invention is particularly preferably a hydrolase protein, which consists of an amino acid sequence wherein, in the amino acid sequence shown in SEQ ID NO. 4, the leucine at amino acid number 70 is substituted with aspartic acid, the leucine at amino acid number 270 is substituted with any one of glutamine, glutamic acid and alanine, the leucine at amino acid number 273 is substituted with arginine, and the leucine at amino acid number 313 is substituted with methionine, and which has activity of catalyzing the reaction represented by the above formula (1) at higher selectivity than the protein consisting of the amino acid sequence shown in SEQ ID NO. 1.

The hydrolase protein of the present invention further includes a hydrolase protein, which consists of an amino acid sequence having homology of 90% or more with the amino acid sequence of the above-described hydrolase protein of the present invention, or an amino acid sequence comprising a substitution, deletion, and/or addition of one or several amino acids with respect to the amino acid sequence of the above-described hydrolase protein of the present invention, and which has activity of catalyzing the reaction represented by the formula (1) at higher selectivity than the protein consisting of the amino acid sequence shown in SEQ ID NO. 1.

In the present invention, the term "homology of 90%" in the description "an amino acid sequence having homology of 90% or more with the amino acid sequence of the above-described hydrolase protein of the present invention" is used to mean that the concerned amino acid sequence has homology or identity of 90% or more, preferably 93% or more, more preferably 95% or more, and particularly preferably 98% or more, with the amino acid sequence of the hydrolase protein of the present invention.

In the present invention, the term "one or several" in the description "a substitution, deletion, and/or addition of one or several amino acids" is used to mean, for example, about 1 to 40, preferably about 1 to 20, more preferably about 1 to 10, and further preferably about 1 to 5 amino acids.

The origin of the hydrolase protein of the present invention is not particularly limited. It may be a natural enzyme derived from microorganisms and the like, or a genetically recombinant protein.

Such a natural enzyme can be preferably obtained from *Bacillus subtilis*. Specifically, the hydrolase protein of the present invention can be obtained from strains such as *Bacillus subtilis* NBRC3026, *Bacillus subtilis* NBRC3108, *Bacillus subtilis* NBRC3027, and *Bacillus subtilis* NBRC3013, by ordinary methods for extracting and purifying enzymes. Specific examples of the extraction method include: extraction methods involving cell disruption, such as fragmentation, homogenization, a sonic treatment, an osmotic shock procedure and a freezing-thawing process; extraction with a surfactant; and a combination of these methods. Specific examples of the purification method include salting-out using ammonium sulfate, sodium sulfate, etc., centrifugation, dialysis, ultrafiltration, adsorption chromatography, ion exchange chromatography, hydrophobic chromatography, reversed phase chromatography, gel filtration, gel permeation chromatography, affinity chromatography, electrophresis, zymography, and a combination of these methods.

A gene of the hydrolase protein of the present invention is cloned according to a known method, and the cloned gene is then introduced into a suitable host to allow it to express therein, so that the hydrolase protein of the present invention can be obtained as a genetically recombinant protein. For example, on the basis of information regarding the nucleotide sequence of a gene encoding the hydrolase protein of the present invention, probes or primers that are specific to the gene of the hydrolase protein of the present invention are designed. Using the probes or primers, a DNA encoding the hydrolase protein of the present invention is isolated or amplified from a DNA library (e.g. a genomic DNA library, a cDNA library, etc.) of *Bacillus subtilis* NBRC3026, *Bacillus subtilis* NBRC3108, *Bacillus subtilis* NBRC3027, *Bacillus subtilis* NBRC3013 or the like. Then, the DNA is inserted into a vector by gene recombination. Thereafter, the vector is introduced into host cells, so that the DNA is expressed therein, thereby obtaining the hydrolase protein of the present invention.

(2) DNA of the Present Invention

According to the present invention, there is provided a DNA encoding the above-described hydrolase protein of the present invention.

Specific examples of the DNA of the present invention include those consisting of the following nucleotide sequences (a), (b), and (c):

(a) the nucleotide sequence shown in any one of SEQ ID NOS. 7 to 10;

(b) a nucleotide sequence of a DNA capable of hybridizing under stringent conditions with the DNA consisting of the nucleotide sequence shown in any one of SEQ ID NOS. 7 to 10, wherein the nucleotide sequence encodes a hydrolase protein having activity of catalyzing the reaction represented by the following formula (1) at higher selectivity than the protein consisting of the amino acid sequence shown in SEQ ID NO. 1; and (c) a nucleotide sequence comprising a substitution, deletion, and/or addition of one or several nucleotides with respect to the nucleotide sequence shown in any one of SEQ ID NOS. 7 to 10, wherein the nucleotide sequence encodes a hydrolase protein having activity of catalyzing the reaction represented by the following formula (1) at higher selectivity than the protein consisting of the amino acid sequence shown in SEQ ID NO. 1:

[Formula 9]

Formula (1)

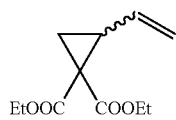 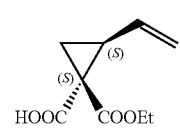

The DNA encoding the hydrolase protein of the present invention is a DNA that is cloned from *Bacillus subtilis* NBRC3026, *Bacillus subtilis* NBRC3108, *Bacillus subtilis* NBRC3027 or *Bacillus subtilis* NBRC3013, or a DNA which is obtained by introducing a mutation to the aforementioned DNA. Since the nucleotide sequence of the concerned DNA has been determined by the present invention, a DNA can also be synthesized based on the determined nucleotide sequence. Furthermore, a DNA can also be isolated from a DNA library (e.g. a genomic DNA library, a cDNA library, etc.) of microorganisms such as *Bacillus subtilis* by hybridization using, as a probe, an oligonucleotide produced based on the determined nucleotide sequence, or by PCR using, as a primer, an oligonucleotide produced based on the determined nucleotide sequence. Still further, the DNA of the hydrolase protein of the present invention may not only be separated from natural microorganisms, but may also be synthesized by a known DNA synthesis method, such as the method described in U.S. Pat. No. 6,472,184 or U.S. Pat. No. 5,750,380.

In the present invention, the "DNA capable of hybridizing under stringent conditions with . . ." means a DNA comprising a nucleotide sequence having homology of 80% or more, preferably 90% or more, and more preferably 95% or more, with the DNA having the nucleotide sequence shown in any one of SEQ ID NOS. 7 to 10 or a complementary sequence thereof, by BLAST analysis. Moreover, the hybridization under stringent conditions can be carried out by a method, which comprises performing a reaction at a temperature from 40° C. to 70° C., and preferably from 60° C. to 65° C. in an ordinary hybridization buffer, and then washing the reaction product in a washing solution having a salt concentration of, for example, 15 mM to 300 mM, and preferably 15 mM to 60 mM.

In the present invention, the term "one or several" in the description "a substitution, deletion, and/or addition of one or several nucleotides" is used to mean, for example, about 1 to 30, preferably about 1 to 20, more preferably about 1 to 10, and further preferably about 1 to 5 nucleotides.

A person skilled in the art can readily select a substitution, deletion, and/or addition of amino acids, which does not substantially affect enzyme activity. In addition, the DNA encoding the hydrolase protein of the present invention having a substitution, deletion, and/or addition of amino acids, which does not substantially affect enzyme activity, can be obtained from a natural mutant strain or a variety, for example.

A DNA having a nucleotide sequence comprising a substitution, deletion, and/or addition of one or several nucleotides with respect to the nucleotide sequence of any one of SEQ ID NOS. 7 to 10 can be produced by ordinary mutation operations such as a method using a mutation inducer or site-directed mutagenesis. These mutation operations can be readily carried out, for example, using commercially available kits such as PrimeSTAR Mutagenesis Basal Kit (Takara Bio Inc.) or QuikChange Site-Directed Mutagenesis Kit (manufactured by Stratagene).

(3) Recombinant Vector and Transformant

According to the present invention, there is further provided a recombinant vector having the DNA of the present invention. In order to prepare a recombinant vector, in general, the DNA of the present invention and a promoter suitable for host microorganisms are inserted into a vector, so that the 5'-terminal side of the coding region of the DNA of the present invention can be ligated to the downstream of the promoter. Alternatively, an expression vector containing a promoter may be used, and the DNA of the present invention may be inserted into the expression vector.

The expression vector is not particularly limited, as long as it can replicate and proliferate in host microorganisms. Examples of such an expression vector include a plasmid vector; a shuttle vector, and a phage vector. Specific examples of the plasmid vector include pBR322, pUC18, pHSG298, pUC118, pSTV28, pTWV228, and pHY300PLK (all of these plasmid vectors are available from, for example, Takara Bio Inc.), and pET Expression Vector Series (manufactured by Novagen). Examples of shuttle vector for the *E. coli*/coryneform bacteria include: the plasmid pCRY30 described in JP Patent Publication (Kokai) No. 3-210184 A (1991); the plasmids pCRY21, pCRY2KE, pCRY2KX, pCRY31, pCRY3KE and pCRY3KX described in JP Patent Publication (Kokai) No. 2-276575 A (1990); the plasmids pCRY2 and pCRY3 described in JP Patent Publication (Kokai) No. 1-191686 A (1989); pAM330 described in JP Patent Publication (Kokai) No. 58-67679 A (1983); pHM1519 described in JP Patent Publication (Kokai) No. 58-77895 A (1983); pAJ655, pAJ611 and pAJ1844 described in JP Patent Publication (Kokai) No. 58-192900; pCG1 described in JP Patent Publication (Kokai) No. 57-134500 A (1982); pCG2 described in JP Patent Publication (Kokai) No. 58-35197 A (1983); pCG4 and pCG11 described in JP Patent Publication (Kokai) No. 57-183799 A (1982), and their derivatives. In addition, an example of the phage vector is a λFixII vector (available from Stratagene).

A promoter possessed by host microorganisms can be generally used as a promoter for the expression of a DNA encoding the hydrolase protein of the present invention. However, the promoter used herein is not limited thereto. The promoter is not particularly limited, as long as it has a nucleotide sequence derived from a prokaryote for initiating transcription of the DNA of the hydrolase protein of the present invention. Specific examples of such a promoter include a lactose operon promoter, a tryptophan operon promoter, a λ phage-derived PL promoter, and a tryptophan-lactose hybrid (tac) promoter [H. A. Bose et al., Proc. Natl. Acad. Sci. U.S.A., Vol. 80, p. 21 (1983)]. Among these promoters, an inducible promoter can also be used for the purpose of improving expression efficiency. For example, in the case of the aforementioned lactose operon promoter, gene expression can be induced by adding lactose or isopropyl-β-D-thiogalactoside (IPTG).

According to the present invention, there is further provided a transformant, which is obtained by introducing the DNA of the present invention or a recombinant vector into host cells. The host, into which the DNA of the present invention or a recombinant vector is to be introduced, is not particularly limited. Hosts, which have activity of hydrolyzing dialkyl 2-vinylcyclopropane-1,1-dicarboxylate to compounds other than (1S,2S)-1-alkoxycarbonyl-2-vinykyclopropanecarboxylic acid, are not preferably used. Moreover, hosts, which have activity of converting the generated (1S, 2S)-1-alkoxycarbonyl-2-vinylcyclopropanecarboxylic acid to another compound, are not preferable, either.

The host that can be used in the present invention can be selected by allowing a host candidate to come into contact with dialkyl 2-vinylcyclopropane-1,1-dicarboxylate or with (1S,2S)-1-alkoxycarbonyl-2-vinylcyclopropanecarboxylic acid as a product of interest, and then analyzing a compound obtained as a result of the contact.

Specific examples of the host microorganisms that can be used in the present invention include bacteria such as *Escherichia* sp. (e.g. *Escherichia coli*). Moreover, bacteria such as *Actinomycetes* sp., *Bacillus* sp., *Serratia* sp., *Pseudomonas* sp., *Corynebacterium* sp., *Brevibacterium* sp., *Rhodococcus* sp., *Lactobacillus* sp., *Streptomyces* sp., *Thermus* sp., and Streptococcus sp., which have the above-described properties, can also be used as hosts, into which the DNA of the present invention or a recombinant vector is to be introduced.

Specific examples of such host microorganisms that can be used herein include *Escherichia coli, Bacillus subtilis, Bacillus brevis, Bacillus stearothermophilus, Serratia marcescens, Pseudomonas putida, Pseudomonas aeruginosa, Corynebacterium glutamicum, Brevibacterium flavum, Brevibacterium lactofermentum, Rhodococcus erythropolis, Thermus thermophilus, Streptococcus lactis, Lactobacillus casei,* and *Streptomyces lividans,* which have the above-described properties.

Furthermore, the above-described microorganisms, which have the activity of hydrolyzing dialkyl 2-vinylcyclopropane-1,1-dicarboxylate to compounds other than (1S,2S)-1-alkoxycarbonyl-2-vinylcyclopropanecarboxylic acid or the activity of converting the generated (1S,2S)-1-alkoxycarbonyl-2-vinylcyclopropanecarboxylic acid to another compound, can be used as hosts, into which the DNA of the present invention or a recombinant vector is to be introduced, by disrupting a gene encoding the enzyme protein having the aforementioned activity by the existing method.

Examples of a method of introducing a gene into the above-described host microorganisms, which can be applied herein, include: transformation methods such as a competent cell method [Journal of Molecular Biology, Vol. 53, p. 159 (1970)] and a pulse wave electrification method [J. Indust. Microbiol., Vol. 5, p. 159 (1990)]; a transduction method using phage [E. Ohtsubo, Genetics, Vol. 64, p. 189 (1970)]; a conjugal transfer method [J. G. C. Ottow, Ann. Rev. Microbiol., Vol. 29, p. 80 (1975)]; and a cell fusion method [M. H. Gabor, J. Bacteriol., Vol. 137, p. 1346 (1979)]. From these methods, a method suitable for host microorganisms may be selected, as appropriate.

In addition to the above-described gene expression method using an expression vector, the gene may also be allowed to express by a homologous recombination technique whereby the DNA encoding the hydrolase protein of the present invention ligated to a promoter is directly introduced into the chromosome of a host microorganism, or by a technique of introducing the gene using transposon, an insertion sequence or the like. Accordingly, the transformant of the present invention is sufficient, as long as the enzyme of the present invention is expressed therein. The method of introducing the gene into a host is not limited.

(4) Production of Hydrolase Protein of the Present Invention Using Transformant

According to the present invention, the transformant obtained as described above may be cultured, and the hydrolase protein of the present invention may be then obtained from the culture.

The transformant can be cultured in an ordinary nutritive medium containing a carbon source, a nitrogen source, inorganic salts, various types of vitamins, etc. Examples of the carbon source used herein include: sugars such as glucose, sucrose, fructose and maltose; alcohols such as ethanol and methanol; organic acids such as citric acid, malic acid, succinic acid, maleic acid and fumaric acid; and blackstrap molasses. As a nitrogen source, ammonia, ammonium sulfate, ammonium chloride, ammonium nitrate, urea and the like are used singly or in combination. Examples of the inorganic salts used herein include potassium monohydrogen phosphate, potassium dihydrogen phosphate, and magnesium sulfate. Other than these substances, nutritive substances such as peptone, meat extract, yeast extract, corn steep liquor, casamino acid, and various types of vitamins such as biotin, may be added to the medium.

The culture is generally carried out under aerobic conditions involving aeration stirring, shaking, or the like. The culture temperature is not particularly limited, as long as it allows host microorganisms to grow. In addition, the pH applied during the culture is not particularly limited, either, as long as it allows host microorganisms to grow. During the culture, the pH value can be adjusted by addition of acid or alkali.

An enzyme can be collected from the culture according to a known collection method, using the activity of the enzyme as an indicator. It is not always necessary to purify the collected enzyme to a homogeneous state. The enzyme may be purified up to a purification degree that depends on intended use.

As a roughly purified fraction or a purified enzyme used in the present invention, there may be used a cell mass separated from cell broth obtained as a result of the cultivation of a transformant; a disrupted product obtained by disrupting the cell broth or the cell mass by means such as ultrasonic wave or friction under pressure; an extract containing the hydrolase protein of the present invention, which is obtained by extracting the disrupted product with water or the like; a crude preparation of the hydrolase protein of the present invention, which is obtained by further performing a treatmentsuch as ammonium sulfate fractionation or column chromatography on the above-described extract; or a purified enzyme preparation. Furthermore, a product obtained by immobilizing the above-described cell mass, disrupted product, extract, roughly purified fraction or purified enzyme on a carrier may also be used.

The above-described cell mass, cell mass disrupted product, extract, or purified enzyme can be immobilized on a suitable carrier such as an acrylamide monomer, alginic acid or carrageenan, according to a known ordinary method of immobilizing such cell mass or the like on a carrier. For example, when the cell mass is immobilized on the carrier, the cell mass, which has just been recovered from the culture or has been washed with a suitable buffer such as an approximately 0.02 to 0.2 M phosphate buffer (pH 6 to 10), can be used.

(5) Production of (1S,2S)-1-Alkoxycarbonyl-2-Vinylcyclopropanecarboxylic Acid Using Hydrolase Protein of the Present Invention According to the present invention, there is provided a production method represented by the following formula (2), namely, a method for producing (1S,2S)-1-alkoxycarbonyl-2-vinylcyclopropanecarboxylic acid, which comprises allowing the hydrolase protein of the present invention to act on dialkyl 2-vinylcyclopropane-1,1-dicarboxylate, so as to produce the (1S,2S)-1-alkoxycarbonyl-2-vinylcyclopropanecarboxylic acid.

[Formula 10]

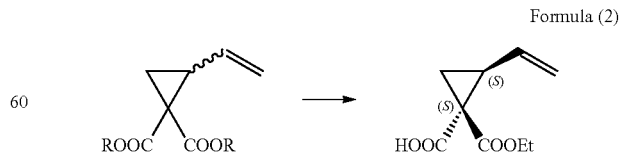

Formula (2)

In the formula (2), R represents an alkyl group containing 1 to 10 carbon atoms, an aralkyl group containing 7 to 20 carbon atoms or an aryl group containing 6 to 12 carbon atoms, each of which may be optionally substituted.

An example of the alkyl group containing 1 to 10 carbon atoms which may be optionally substituted, which is represented by R, is a substituted or unsubstituted, linear, branched or cyclic alkyl group containing 1 to 10 carbon atoms. A substituted or unsubstituted, linear, branched or cyclic alkyl group containing 1 to 6 carbon atoms is more preferable. Among these groups, preferred examples include a methyl group, an ethyl group, an isopropyl group, a normal propyl group, a normal butyl group, an isobutyl group, a sec-butyl group, a tert-butyl group, a normal pentyl group, an isopentyl group, a tert-pentyl group, a neopentyl group, a normal hexyl group, a cyclopropyl group, a cyclobutyl group, a cyclopentyl group, and a cyclohexyl group. An alkyl group containing 1 to 4 carbon atoms is particularly preferable.

The aralkyl group containing 7 to 20 carbon atoms which may be optionally substituted, which is represented by R, is preferably a substituted or unsubstituted aralkyl group containing 7 to 12 carbon atoms. Among these groups, preferred examples include a benzyl group, a 4-methylbenzyl group, a 4-methoxybenzyl group, a 4-chlorobenzyl group, a 4-bromobenzyl group, a 2-phenylethyl group, a 1-phenylethyl group, and a 3-phenylpropyl group.

Examples of the aryl group containing 6 to 12 carbon atoms which may be optionally substituted, which is represented by R, include a phenyl group, a 1-naphthyl group, a 2-naphthyl group, an o-methylphenyl group, a m-methylphenyl group, a p-methylphenyl group, an o-methoxyphenyl group, a m-methoxyphenyl group, a p-methoxyphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3,5-trimethylphenyl group, a 2,3,6-trimethylphenyl group, a 2,4,6-trimethylphenyl group, an o-nitrophenyl group, a m-nitrophenyl group, and a p-nitrophenyl group.

R is preferably a methyl group, an ethyl group, a tert-butyl group, or a benzyl group, and is more preferably an ethyl group.

When the hydrolase protein of the present invention is allowed to act on dialkyl 2-vinylcyclopropane-1,1-dicarboxylate, a purified or roughly purified hydrolase protein of the present invention, a microorganism that generates the hydrolase protein of the present invention (e.g. a transformant having a DNA encoding the hydrolase protein of the present invention, etc.), or a treated product thereof, is allowed to act on the dialkyl 2-vinylcyclopropane-1,1-dicarboxylate, so as to produce (1S,2S)-1-alkoxycarbonyl-2-vinylcyclopropanecarboxylic acid.

The reaction method is not particularly limited. Dialkyl 2-vinylcyclopropane-1,1-dicarboxylate used as a substrate is added to a liquid containing the hydrolase protein of the present invention, and the reaction can be then carried out at an appropriate temperature (e.g. approximately 10° C. to 40° C.) or under an appropriate pressure (e.g. around atmospheric pressure). Thereby, (1S,2S)-1-alkoxycarbonyl-2-vinylcyclopropanecarboxylic acid can be produced.

The method of fractionating the (1S,2S)-1-alkoxycarbonyl-2-vinylcyclopropanecarboxylic acid of interest from the reaction mixture is not particularly limited. A separation or purification method that is known to a person skilled in the art can be applied. Examples of the applicable separation or purification method include, but are not limited, solvent extraction, crystallization, resin adsorption, and column chromatography.

The hydrolase protein of the present invention can be particularly preferably used in a method of hydrolyzing diethyl 2-vinylcyclopropane-1,1-dicarboxylate to produce (1S,2S)-1-ethoxycarbonyl-2-vinylcyclopropanecarboxylic acid.

Moreover, the dialkyl 2-vinylcyclopropane-1,1-dicarboxylate of the present invention can be produced by the reaction represented by the following formula (3):

[Formula 11]

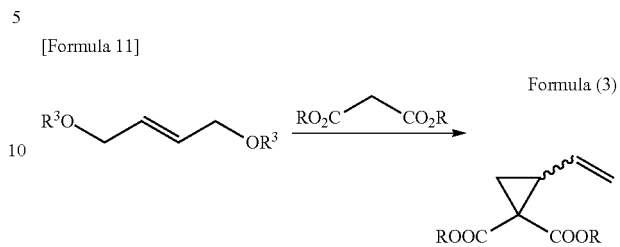

Formula (3)

Specifically, the raw material compound of the formula (3) is allowed to react with a malonic ester in the presence of an alkali metal alkoxide or alkali metal hydride, so as to produce the dialkyl 2-vinylcyclopropane-1,1-dicarboxylate of the present invention.

In the formula (3), wherein $R^3$ represents an arylsulfonyl group containing 6 to 12 carbon atoms, an alkylsulfonyl group containing 1 to 10 carbon atoms or an aralkylsulfonyl group containing 7 to 20 carbon atoms, each of which may be optionally substituted. Examples of $R^3$ include a benzenesulfonyl group, a p-toluenesulfonyl group, a 1-naphthalenesulfonyl group, a 2-naphthalenesulfonyl group, a methanesulfonyl group, an ethanesulfonyl group, a propanesulfonyl group, a trifluoromethanesulfonyl group, and a benzylsulfonyl group. $R^3$ is preferably a methanesulfonyl group, a benzenesulfonyl group, and a p-toluenesulfonyl group. Among these groups, a p-toluenesulfonyl group is particularly preferable. And, R has the same definitions as those described above.

Herein, the raw material compound of the formula (3) can be produced according to a known method, such as the method described in Frederic Dolle et al., Bioorg. Med. Chem. 2006, 14, 1115-1125, etc. Otherwise, the raw material compound of the formula (3) can also be produced by the reaction represented by the following formula (4):

[Formula 12]

$$X^1 \diagdown O \diagup\diagdown\diagdown\diagup\diagdown O \diagdown X^2 \longrightarrow$$

$$HO \diagdown\diagup\diagdown\diagdown\diagup\diagdown OH \longrightarrow$$

$$R^3O \diagdown\diagup\diagdown\diagdown\diagup\diagdown OR^3 \xrightarrow{\text{Crystallization}}$$

$$R^3O \diagdown\diagup\diagdown OR^3$$

Formula (4)

Specifically, 1,4-butenediol is allowed to react with the compound represented by $R^3X$, followed by crystallization, so as to produce the raw material compound of the formula (3). Alternatively, a commercially available raw material compound is hydrolyzed with an acid or a base to obtain 1,4-butenediol, and the obtained 1,4-butenediol is then allowed to react with the compound represented by $R^3X$, followed by crystallization, so as to produce the raw material compound of the formula (3).

In the formula (4), $X^1$ represents a hydrogen atom or $R^1$, and $X^2$ represents a hydrogen atom or $R^2$, wherein $R^1$ and $R^2$ each independently represent an alkylcarbonyl group containing 2 to 11 carbon atoms, an aralkylcarbonyl group containing 8 to 21 carbon atoms or an arylcarbonyl group containing 7 to 13 carbon atoms, each of which may be optionally substituted, provided that $X^1$ and $X^2$ do not simultaneously represent hydrogen atoms. Preferably, $X^1$ is $R^1$, and $X^2$ is $R^2$. More preferably $R^1$ and $R^2$ each represent an acetyl group, an ethylcarbonyl group, a tert-butylcarbonyl group, or a benzoyl group. Further preferably, $R^1$ and $R^2$ each represent an acetyl group.

Using the (1S,2S)-1-ethoxycarbonyl-2-vinylcyclopropanecarboxylic acid obtained in the present invention, there can be produced (1R,2S)/(1S,2R)-1-amino-1-ethoxycarbonyl-2-vinylcyclopropane that is an intermediate useful for the production of various types of HCV NS3 protease inhibitors and the like, which are currently under development as therapeutic agents for hepatitis C, and a salt thereof.

The present invention will be described more in detail in the following examples. However, these examples are not intended to limit the scope of the present invention.

EXAMPLES

Example 1

Cloning of para-Nitrobenzyl Esterase Gene (pnbA; SEQ ID NOS. 6 to 10)

(1) Gene Cloning

*Bacillus subtilis* ATCC23857, *Bacillus subtilis* NBRC3026, *Bacillus subtilis* NBRC3108, *Bacillus subtilis* NBRC3027, and *Bacillus subtilis* NBRC3013 were each cultured overnight in liquid media designated by their culture collection institutes. Thereafter, a chromosomal DNA was prepared from each of the obtained cell masses, using DNeasy Blood & Tissue Kit (manufactured by QIAGEN).

Based on a gene sequence (hereinafter referred to as pnbA23857, SEQ ID NO. 6) encoding para-nitrobenzyl esterase derived from *Bacillus subtilis* ATCC23857 whose genome sequence had been known (hereinafter referred to as PNBE23857, GenBank Accession No. ZP_03593235, SEQ ID NO. 1), primers for amplifying a full-length para-nitrobenzyl esterase gene, pnbA F and pnbA R were designed and synthesized. The nucleotide sequences of the two primers are shown in SEQ ID NO. 11 (pnbA F) and SEQ ID NO. 12 (pnbA R) in the sequence listing, respectively.

Using, as a template, each of the chromosomal DNAs prepared from the individual strains, and also using pnbA F and pnbA R as primers, a DNA fragment with a size of approximately 1.5 kbp was amplified by a polymerase chain reaction (PCR).

In this PCR, the reaction was carried out using Easy-A High Fidelity PCR Cloning Enzyme (manufactured by Agilent Technologies) under the conditions described in instruction manuals included with the kit. As for temperature conditions, after retention at 94° C. for 2 minutes, a cycle (94° C., 30 seconds; 50° C., 30 seconds; and 72° C., 90 seconds) was repeated 35 times, and the reaction product was then retained at 72° C. for 5 minutes, before termination of the reaction.

(2) Preparation of Expression Vector

Using, as a template, the plasmid pKV32 that had been prepared according to the method described in JP Patent Publication (Kokai) No. 2005-34025 A, and also using the primer (pKVXmaIFW) shown in SEQ ID NO. 19 and the primer (pKVXmaIRV) shown in SEQ ID NO. 20, a fragment with a size of approximately 4 kbp was amplified by PCR. The amplified fragment was digested with the restriction enzyme XmaI, and thereafter, using Ligation-Convenience Kit (manufactured by Nippon Gene Co., Ltd.), it was subjected to self ligation to obtain a plasmid. The obtained plasmid was named as pKW32.

In this PCR, the reaction was carried out using KOD-plus-Ver. 2 (manufactured by Toyobo Co., Ltd.) under the conditions described in instruction manuals included with the kit. As for temperature conditions, after retention at 94° C. for 2 minutes, a cycle (94° C., 15 seconds; 58° C., 30 seconds; and 68° C., 4 minutes) was repeated 30 times, and the reaction product was then retained at 68° C. for 5 minutes, before termination of the reaction.

(3) Preparation of Expression Plasmid

Using Ligation-Convenience Kit (manufactured by Nippon Gene Co., Ltd.), the DNA fragments obtained in (1) above were each inserted into the cloning vector pKW32 prepared in (2) above. Hereinafter, the obtained plasmids were referred to as ppnbA23857, ppnbA3026, ppnbA3108, ppnbA3027, and ppnbA3013.

With regard to the plasmids ppnbA3026, ppnbA3108, ppnbA3027, and ppnbA3013, the DNA sequences that had been inserted into them were analyzed, and as a result, it was confirmed that they each contained a gene consisting of 1467-bp ORE The obtained genes were named as pnbA3026, pnbA3108, pnbA3027, and pnbA3013, respectively. The DNA sequences of these genes were as shown in SEQ ID NOS. 7 (pnbA3026), 8 (pnbA3108), 9 (pnbA3027), and 10 (pnbA3013), respectively. The amino acid sequences encoded by these DNA sequences were named as PNBE3026, PNBE3108, PNBE3027, and PNBE3013, respectively. These amino acid sequences were as shown in SEQ ID NOS. 2 (PNBE3026), 3 (PNBE3108), 4 (PNBE3027), and 5 (PNBE3013), respectively. These amino acid sequences showed sequence identity of 97%, 91%, 90%, and 98%, respectively, with the amino acid sequence (SEQ ID NO. 1) of the known PNBE23857.

Example 2

Comparison of Selectivity of Novel Para-Nitrobenzyl Esterase

Using the 5 types of plasmids obtained in Example 1, *Escherichia coli* JM109 (manufactured by Takara Bio Inc.) was transformed according to an ordinary method. The obtained recombinant *Escherichia coli* were each subjected to a shaking culture at 30° C. in a liquid LB medium containing 20 mg/l kanamycin and 0.2 mM IPTG. On the $20^{th}$ hour of the culture, cells were collected.

The obtained cell mass was reacted in a 100 mM potassium phosphate buffer containing a 5 g/l racemic form of 1,1-diethoxycarbonyl-2-vinylcyclopropane (hereinafter referred to as "VCPDE") and 5% dimethyl sulfoxide at 30° C. at pH 7 for 21 hours.

After completion of the reaction, the reaction solution was analyzed by high performance liquid chromatography (HPLC) under the following conditions.

Column: CHIRALPAK AD-3 (4.6×250 mm, manufactured by Daicel Corporation)
Eluent:hexane:ethanol:trifluoroacetic acid=95:5:0.1
Flow rate: 0.8 ml/min
Temperature: 30° C.
Detection: UV 210 nm As a result of the analysis, generation of 1-ethoxycarbonyl-2-vinylcyclopropanecarboxylic acid (hereinafter referred to as "VCPME") was confirmed. Based on the obtained results, the "1R2S/1S2S ratio" that indicates the ratio between the (1S,2S) form and the (1R,2S) form in the generated VCPME, the "1S2S form optical purity" that indicates the enantiomer excess of the (1S,2S) form to the (1R,2R) form, and the "1S2R/1S2S ratio" that indicates the ratio between the (1S, 2S) form and the (1S,2R) form, which were to be used as indicators of selectivity, were obtained. The results are summarized in Table 1. Moreover, the hydrolytic activity of the concerned substrate was not observed in a cell mass that had been transformed with only the plasmid pKW32. All of the enzymes exhibited a sufficiently low value of the "1R2S/1S2S ratio."

The three types of enzymes, PNBE3026, PNBE3108, and PNBE3027, exhibited a higher value of the "1S2S form optical purity" than that of the enzyme PNBE23857 whose sequence had been known.

Moreover, the enzyme PNBE3013 exhibited a lower value of the "1S2R/1S2S ratio" than that of the enzyme PNBE23857 whose sequence had been known.

TABLE 1

| Enzyme Name | 1R2S/1S2S Ratio | 1S2S Form Optical Purity (% e.e.) | 1S2R/1S2S Ratio | Remarks |
|---|---|---|---|---|
| PNBE23857 | 0.0222 | 93.1 | 0.953 | Reference Example |
| PNBE3026 | 0.0263 | 94.2 | 0.970 | The present Invention |
| PNBE3108 | 0.0504 | 97.0 | 1.01 | The present Invention |
| PNBE3027 | 0.0404 | 97.4 | 0.998 | The present Invention |
| PNBE3013 | 0.0433 | 89.2 | 0.863 | The present Invention |

Synthesis Example

The VCPDE used in Example 1 was synthesized as follows.

93.4 g (583 mmol) of malonic acid diethyl ester and 1000 mL of toluene were added into a four-necked flask (2 L), and thereafter, 223 mL (569 mmol) of a 20% sodium ethoxide ethanol solution was added thereto as a base. The obtained mixture was stirred at room temperature for 1.5 hours, and 59.4 g of trans-1,4-dibromo-2-butene (278 mmol; a reagent manufactured by Sigma-Aldrich) was then added to the reaction solution. The obtained mixture was stirred at room temperature for 2 hours, and 109 mL (278 mmol) of a 20% sodium ethoxide ethanol solution was then added to the reaction solution. The obtained mixture was stirred at room temperature for 1 hour, and 29.1 g of trans-1,4-dibromo-2-butene (136 mmol; a reagent manufactured by Sigma-Aldrich) was then added to the reaction solution. The mixture was stirred at room temperature for 4 hours, and 347 mL of a 1 M sodium hydroxide aqueous solution was then added to the reaction solution. The mixture was stirred for 14 hours, and an organic layer was then separated. Subsequently, the organic layer was washed with 132 mL of water twice, and was then dried over anhydrous sodium sulfate. The resultant was filtrated, and the obtained filtrate was concentrated at 40° C. under reduced pressure, so as to obtain 99.3 g of 1,1-di-ethoxycarbonyl-2-vinylcyclopropane in the form of a crude product of a light yellow oily substance. This crude product contained 83.2 g of 1,1-di-ethoxycarbonyl-2-vinylcyclopropane (yield: 94.9%). However, this crude product did not contain a malonic diethyl ester.

Example 3

Three-Dimensional Structure Modeling of Hydrolase Protein of the Present Invention (SEQ ID NO. 4)

A BLAST search was performed against Protein Data Bank (PDB) for the amino acid sequence of PNBE3027. Three types of crystal structures as described below were selected as reference structures. It is to be noted that the notation "A56V" indicates that the amino acid residue at position 56, alanine (A), is substituted with valine (V).
para-Nitrobenzyl esterase Mutation: A56V, I60V, T73K, L144M, L313F, H322Y, A343V, M358V, Y370F, A400T, G412E, I437T, T459S (PDB id: 1C7J); sequence identity: 89%
para-Nitrobenzyl esterase Mutation: I60V, L144M, P317S, H322R, L334S, M358V, Y370F (PDB id: 1C7I); sequence identity: 90%
para-Nitrobenzyl esterase (PDB id: 1QE3); sequence identity: 91%

A homology model was produced using Discovery Studio Modeling (hereinafter abbreviated as DS Modeling) Ver. 2.5. With regard to the obtained initial modeling structure, CHARMM (Chemistry at Harvard Macromolecular Mechanics) force yield was assigned to each atom, and structural optimization was then performed based on molecular mechanics calculation. For such structural optimization, 1000 steps of calculation were performed by the Steepest Decent method, and then, 5000 steps of calculation were performed by the Adapted Basis Newton-Raphson method.

A substrate complex model was produced by coordinating an S form and an R form of VCPDE, which served as a substrate, in the direction of generating (1S,2S)-VCPME and in the direction of generating (1R,2R)-VCPME, respectively, with respect to the obtained homology model, thereby creating an initial structure, and then performing energy minimization. When such energy minimization was performed, the following distance constraint conditions were determined, while taking into consideration the hydrolytic reaction mechanism of esterase.
The distance between the nitrogen atoms of three amides (Gly106, Ala107, Ala190) which forms an oxyanion hole and the carbonyl oxygen of an ester bond to be hydrolyzed, is set not less than 2.0 Å and not more than 3.0 Å.
The distance between the alcohol oxygen atom of the active site Ser189 and the carbonyl carbon of an ester bond to be hydrolyzed is set not less than 2.0 Å and not more than 3.0 Å.

The structures obtained by the aforementioned treatments were defined as a "1S2S model" and a "1R2R model."

Example 4

Assumption of Amino Acid Residues Associated with Recognition of Substrates in Para-Nitrobenzyl Esterase First, all of amino acid residues that were partially or entirely present within 8 Å from the carbon atom at position 2 of a vinyl group of VCPDE were extracted from each of the "1S2S model" and the "1R2R model," obtained in Example 3. Discovery Studio Visualizer v2.5.5.9350 was used to calculate the distance. The distance from an atom other than a hydrogen atom which was closest to the carbon atom at position of the vinyl group of VCPDE in each model in the extracted each amino acid residue, was defined as the distance from each amino acid residue. With regard to each of the extracted amino acid residues, the above-defined distance in the "1S2S model" was compared with the above-defined distance in the "1R2R model." As a result, amino acid residues, in which the distance in the "1S2S model" is closer than the distance in the "1R2R model," are shown in Table 2, and amino acid residues, in which the distance in the "1R2R model" is closer than the distance in the "1S2S model," are shown in Table 3.

From the aforementioned results, it is assumed that, in the case of the amino acid residues shown in Table 2, the modified amino acid residues whose side chains have lower bulkiness than that of wild-type amino acids are able to exhibit advantageous selectivity towards generation of the (1S,2S) form of VCPME, and that in the case of the amino acid residues shown in Table 3, the modified amino acid residues whose side chains have higher bulkiness than that of wild-type amino acids are able to exhibit such advantageous selectivity.

TABLE 2

| Amino Acid Residue | Position | 1S2S Form Model | | 1R2R Form Model | |
| --- | --- | --- | --- | --- | --- |
| | | Distance (Å) | Target Atom | Distance (Å) | Target Atom |
| GLY | 106 | 7.11 | C | 7.43 | C |
| ALA | 107 | 5.05 | CB | 5.76 | CB |
| PHE | 108 | 6.39 | CE2 | 7.44 | CE2 |
| ARG | 219 | 6.44 | CG | 7.16 | NE |
| LEU | 270 | 7.98 | O | | |
| PHE | 271 | 4.13 | O | 4.66 | O |
| GLN | 272 | 5.57 | O | 6.48 | OE1 |
| LEU | 273 | 3.35 | CD2 | 4.70 | CD2 |
| LEU | 274 | 7.46 | N | | |
| PHE | 275 | 7.47 | O | | |
| GLN | 276 | 7.38 | OE1 | | |

TABLE 3

| Amino Acid Residue | Position | 1S2S Form Model | | 1R2R Form Model | |
| --- | --- | --- | --- | --- | --- |
| | | Distance (Å) | Target Atom | Distance (Å) | Target Atom |
| GLU | 188 | | | 7.48 | OE2 |
| ALA | 190 | 6.12 | N | 6.09 | N |
| MET | 193 | 3.75 | CE | 3.61 | CE |
| SER | 215 | 7.15 | O | 6.03 | O |
| GLY | 216 | 7.33 | CA | 6.67 | CA |
| ALA | 217 | 7.90 | N | 7.62 | N |
| PHE | 314 | 4.95 | CZ | 3.94 | CZ |
| MET | 358 | | | 7.40 | O |
| LEU | 362 | 3.64 | CD2 | 3.18 | CD2 |
| PHE | 363 | 4.71 | CZ | 3.36 | CZ |

In Table 2 and Table 3, the abbreviations of the target atoms (the atoms in the amino acid residues) are described according to the method determined by the Protein Data Bank (PDB). Several examples will be given below.
CA=Carbon, Alpha
CB=Carbon, Beta
CG=Oxygen, Gamma
CD=Carbon, Delta
CE=Carbon, Epsilon
CZ=Carbon, Zeta
OE=Oxygen, Epsilon Example 5

Modification of Para-Nitrobenzyl Esterase Gene by Mutation Introduction

Using the plasmid ppnbA3027 obtained in Example 1 as a template, and also using the primer (L70FW) shown in SEQ ID NO. 13 in the sequence listing and the primer (L70RV) shown in SEQ ID NO. 14 in the sequence listing, QuikChange Multi Site-Directed Mutagenesis Kit (manufactured by Stratagene) was employed to introduce random mutation into a nucleotide encoding the leucine at amino acid position 70 in the aforementioned plasmid. The obtained approximately 200 colonies were each subjected to a shaking culture at 30° C. in a liquid LB medium containing 20 mg/l kanamycin and 0.2 mM IPTG, and on the 20$^{th}$ hour of the culture, cells were collected.

The obtained cell mass was reacted in a 100 mM potassium phosphate buffer containing a 5 g/l or 30 g/l racemic form of VCPDE and 5% dimethyl sulfoxide at 30° C. at pH 7 for 21 hours.

Moreover, in the same way, using the primer (L313FW) shown in SEQ ID NO. 15 in the sequence listing and the primer (L313RV) shown in SEQ ID NO. 16 in the sequence listing, random mutation was introduced into a nucleotide encoding the leucine residue at amino acid number 313 in the aforementioned plasmid, and the obtained approximately 200 colonies were then reacted by the same method as that described above.

Furthermore, in the same way, using the primer (L270L273FW) shown in SEQ ID NO. 17 in the sequence listing and the primer (L270L273RV) shown in SEQ ID NO. 18 in the sequence listing, random mutation was introduced into nucleotides encoding the leucine residues at amino acid numbers 270 and 273 in the aforementioned plasmid. The obtained approximately 400 colonies were then reacted by the same method as that described above.

After completion of the reaction, the reaction solution was analyzed by HPLC, applying the same method and conditions as those in Example 2. The results regarding the reaction of each mutant strain, when the concentration of VCPDE as a substrate was set at 5 g/l, are shown in Table 4. The results regarding the reaction of each mutant strain, when the concentration of VCPDE as a substrate was set at 30 g/l, are shown in Table 5. With regard to the obtained clones, a plasmid DNA was extracted from each clone according to an ordinary method, and the DNA sequence thereof was then analyzed. As a result of the analysis, the amino acid residues in the mutation-introduced sites after completion of the mutation are shown in Table 4 and 5.

As a result of a comparison made among No. 1 and Nos. 3 to 6 and 11 in Table 4, it was found that, when the leucine at amino acid number 70 was substituted with any one of aspartic acid, asparagine, serine, threonine, and glycine, the optical purity of the (1S,2S) form of the generated VCPME was improved. In addition, as a result of a comparison made between No. 1 as a wild type and Nos. 2, 7 and 13, it was also found that, when the leucine at amino acid number 313 was substituted with any one of methionine, alanine, and proline, the optical purity of the (1S,2S) form of the generated VCPME was improved. Moreover, it was found that in the case of Nos. 8, 10 and 15, the 1R2S/1S2S ratio in the generated VCPME was improved rather than that of a wild type by simultaneously substituting the leucine residues at amino acid numbers 70 and 313.

Subsequently, as a result of a comparison between No. 1 of Table 4 and No. 16 of Table 5, it was confirmed that the 1S2S form optical purity was decreased by increasing the concentration of VCPDE as a substrate from 5 g/l to 30 g/l. Accordingly, it was clarified that the effect of the introduced mutation needs to be observed in the same substrate concentration. Moreover, as a result of a comparison between Nos. 19, 21 to 25 and No. 16 as a wild type in Table 5, it was confirmed that all of the 1R2S/1S2S ratio, 1S2S form optical purity, and 1S2R/1S2S ratio were improved by substituting the leucine at amino acid number 270 and the leucine at amino acid number 273 with other amino acid residues.

TABLE 4

| No. | L70 | L270 | L273 | L313 | 1R2S/1S2S Ratio | 1S2S Form Optical Purity (% e.e.) | 1S2R/1S2S Ratio |
|---|---|---|---|---|---|---|---|
| 1 |   |   |   |   | 0.0404 | 97.4 | 1.00 |
| 2 |   |   |   | P | 0.0315 | 97.7 | 1.01 |
| 3 | G |   |   |   | 0.0302 | 97.8 | 0.992 |
| 4 | T |   |   |   | 0.0298 | 97.8 | 0.995 |
| 5 | S |   |   |   | 0.0296 | 97.8 | 1.00 |
| 6 | N |   |   |   | 0.0293 | 97.9 | 1.00 |
| 7 |   |   |   | A | 0.0379 | 97.9 | 1.00 |
| 8 | N |   |   | M | 0.0213 | 97.9 | 1.00 |
| 9 | D |   |   | A | 0.0279 | 98.0 | 1.01 |
| 10 | S |   |   | M | 0.0224 | 98.0 | 1.00 |
| 11 | D |   |   |   | 0.0260 | 98.0 | 0.993 |
| 12 | N |   |   | A | 0.0307 | 98.0 | 1.01 |
| 13 |   |   |   | M | 0.0262 | 98.0 | 0.986 |
| 14 | S |   |   | A | 0.0309 | 98.2 | 1.01 |
| 15 | D |   |   | M | 0.0211 | 98.2 | 1.00 |

TABLE 5

| No. | L70 | L270 | L273 | L313 | 1R2S/1S2S Ratio | 1S2S Form Optical Purity (% e.e.) | 1S2R/1S2S Ratio |
|---|---|---|---|---|---|---|---|
| 16 |   |   |   |   | 0.0391 | 95.5 | 0.944 |
| 17 |   |   |   | M | 0.0373 | 96.1 | 1.02 |
| 18 | D |   |   |   | 0.0395 | 96.6 | 1.01 |
| 19 |   | F | H |   | 0.00436 | 96.7 | 0.704 |
| 20 | D |   |   | M | 0.0247 | 97.0 | 1.07 |
| 21 |   | T | R |   | 0.00458 | 97.1 | 0.692 |
| 22 |   | G | R |   | 0.00536 | 97.8 | 0.748 |
| 23 |   | S | R |   | 0.00503 | 98.3 | 0.420 |
| 24 |   | A | R |   | 0.00518 | 98.4 | 0.473 |
| 25 |   | E | R |   | 0.00375 | 98.8 | 0.310 |
| 26 | D | Q | R | M | 0.0973 | 98.9 | 0.461 |

Individual symbols used in Table 4 and Table 5 represent the following.
P: Proline
G: Glycine
T: Threonine
S: Serine
N: Asparagine
A: Alanine
M: Methionine
D: Aspartic acid
F: Phenylalanine
H: Histidine
R: Arginine
E: Glutamic acid
Q: Glutamine Moreover, SEQ ID NOS. 1 to 20 in the present specification are defined as follows.

SEQ ID NO. 1: the amino acid sequence of the para-nitrobenzyl esterase derived from *Bacillus subtilis* ATCC23857 (PNBE23857, GenBank Accession No. ZP_03593235)

SEQ ID NO. 2: the amino acid sequence PNBE3026 of the hydrolase protein derived from *Bacillus subtilis* NBRC3026

SEQ ID NO. 3: the amino acid sequence PNBE3108 of the hydrolase protein derived from *Bacillus subtilis* NBRC3108

SEQ ID NO. 4: the amino acid sequence PNBE3027 of the hydrolase protein derived from *Bacillus subtilis* NBRC3027

SEQ ID NO. 5: the amino acid sequence PNBE3013 of the hydrolase protein derived from *Bacillus subtilis* NBRC3013

SEQ ID NO. 6: the gene sequence (pnbA23857) encoding the para-nitrobenzyl esterase derived from *Bacillus subtilis* ATCC23857 (PNBE23857, GenBank Accession No. ZP_03593235, SEQ ID NO. 1)

SEQ ID NO. 7: the nucleotide sequence pnbA3026 of a DNA encoding the hydrolase protein derived from *Bacillus subtilis* NBRC3026

SEQ ID NO. 8: the nucleotide sequence pnbA3108 of a DNA encoding the hydrolase protein derived from *Bacillus subtilis* NBRC3108

SEQ ID NO. 9: the nucleotide sequence pnbA3027 of a DNA encoding the hydrolase protein derived from *Bacillus subtilis* NBRC3027

SEQ ID NO. 10: the nucleotide sequence pnbA3013 of a DNA encoding the hydrolase protein derived from *Bacillus subtilis* NBRC3013

SEQ ID NO. 11: the primer pnbA F used to amplify a full-length para-nitrobenzyl esterase gene SEQ ID NO. 12: the primer pnbA R used to amplify a full-length para-nitrobenzyl esterase gene SEQ ID NO. 13: primer (L70FW)
SEQ ID NO. 14: primer (L70RV)
SEQ ID NO. 15: primer (L313FW)
SEQ ID NO. 16: primer (L313RV)
SEQ ID NO. 17: primer (L270L273FW)
SEQ ID NO. 18: primer (L270L273RV)
SEQ ID NO. 19: primer (pKVXmaIFW)
SEQ ID NO. 20: primer (pKVXmaJRV)

What is claimed is:

1. A method for producing (1S,2S)-1-alkoxycarbonyl-2-vinylcyclopropanecarboxylic acid, which comprises contacting dialkyl 2-vinylcyclopropane-1,1-dicarboxylate with a hydrolase protein to produce (1S,2S)-1-alkoxycarbonyl-2-vinylcyclopropanecarboxylic acid, wherein the hydrolase protein is capable of catalyzing the following reaction at higher selectivity than the protein consisting of the amino acid sequence shown in SEQ ID NO: 1:

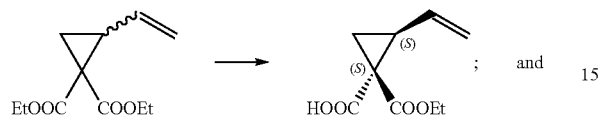

comprises an amino acid sequence shown in any one of SEQ ID NOs: 2 to 5.

2. A method for producing (1S,2S)-1-alkoxycarbonyl-2-vinylcyclopropanecarboxylic acid, which comprises contacting dialkyl 2-vinylcyclopropane-1,1-dicarboxylate with a hydrolase protein to produce (1S,2S)-1-alkoxycarbonyl-2-vinylcyclopropanecarboxylic acid, wherein the hydrolase protein consists of an amino acid sequence shown in any one of SEQ ID NOs: 2 to 5.

* * * * *